(12) United States Patent
Mueller

(10) Patent No.: US 6,981,418 B1
(45) Date of Patent: Jan. 3, 2006

(54) SCANNING ACOUSTIC MICROSCOPY

(75) Inventor: Dennis William Mueller, Lake Dallas, TX (US)

(73) Assignee: MetScan Technologies, LLC, Savannah, GA (US)

( * ) Notice: Subject to any disclaimer, the term of this patent is extended or adjusted under 35 U.S.C. 154(b) by 93 days.

(21) Appl. No.: 10/159,547

(22) Filed: May 31, 2002

Related U.S. Application Data

(60) Provisional application No. 60/378,450, filed on May 7, 2002, provisional application No. 60/355,649, filed on Feb. 8, 2002, and provisional application No. 60/355,201, filed on Feb. 8, 2002.

(51) Int. Cl.
*G01N 9/24* (2006.01)

(52) U.S. Cl. .............. 73/633; 73/618; 73/627
(58) Field of Classification Search ........... 73/633, 73/596, 618, 626, 627, 644
See application file for complete search history.

(56) References Cited

U.S. PATENT DOCUMENTS

| | | | |
|---|---|---|---|
| 2,427,348 A | 9/1947 | Bond et al. ............ 367/157 |
| 2,707,755 A | 5/1955 | Hardie et al. ............ 310/327 |
| 2,881,336 A | 4/1959 | Elion ............ 310/327 |
| 3,663,842 A | 5/1972 | Miller ............ 310/8.3 |
| 4,741,212 A * | 5/1988 | Rehwald ............ 73/600 |
| 4,866,986 A | 9/1989 | Cichanski ............ 73/600 |
| 4,886,986 A | 12/1989 | Watanabe ............ 307/353 |
| 5,046,363 A | 9/1991 | Moore ............ 73/588 |
| 5,307,680 A | 5/1994 | Drescher-Krasicka ....... 73/606 |
| 5,406,849 A | 4/1995 | Drescher-Krasicka et al. ............ 73/588 |
| 5,549,003 A | 8/1996 | Drescher-Krasicka ....... 73/606 |
| 5,599,003 A | 2/1997 | Seemann et al. ......... 251/30.03 |
| 5,627,320 A | 5/1997 | Moore ............ 73/606 |
| 5,641,906 A | 6/1997 | Moore ............ 73/614 |
| 5,712,701 A * | 1/1998 | Clementi et al. ......... 356/237.2 |
| 5,814,731 A * | 9/1998 | Alexander et al. ............ 73/644 |
| 5,827,970 A | 10/1998 | Poku et al. ............ 73/620 |
| 6,089,095 A | 7/2000 | Yang et al. ............ 73/600 |
| 6,092,420 A * | 7/2000 | Kimura et al. ............ 73/620 |
| 6,374,675 B1 | 4/2002 | DePetrillo ............ 73/610 |
| 6,382,028 B1 * | 5/2002 | Wooh et al. ............ 73/602 |

OTHER PUBLICATIONS

Report entitled Corrosion Detection on C/KC–135 Lap Seams Using the Mobile Automated Scanner (MAUS) by David Campbell; at The Third Joint FAA / DoD / NASA Conference on Aging Aircraft Sep. 20–23, 1999, slides 1–27.

Article entitled "A Magnetic Story" by Maya Wagle, Discovery Stock, The Red Chip Review®, dated Mar. 10, 2000; pp. 1–2.

(Continued)

*Primary Examiner*—Hezron Williams
*Assistant Examiner*—Jacques M. Saint-Surin
(74) *Attorney, Agent, or Firm*—Thomas, Kayden, Horstemeyer & Risley L.L.P.

(57) ABSTRACT

A system uses reflection mode acoustical scanning of an object to examine the internal characteristics of the object. The system includes a controller and a jig removably attached to the object. The jig includes an acoustic transducer assembly that is in communication with the controller, which controls the positioning of the acoustic transducer assembly. The jig is adapted to enable the controller to scan the acoustic transducer assembly over the object and to adjust the position of the acoustic transducer assembly during the scan to compensate for the contour of the scanned portion of the object.

32 Claims, 13 Drawing Sheets

OTHER PUBLICATIONS

Web Page entitled "97–03–21 Mary Schiavo, Former FAA Inspector, Joins Faculty" dated Dec. 23, 2001, p. 1; http://www.osu.edu/.../97–03–21 Mary Schiavo%2C Former FAA Inspector%2C Joins Facult.

Web Page entitled "Eddy Current" by Apex Inspections, Inc., Corporate Member of the American Society for Non–Destructive Testing Since 1999, dated Feb. 15, 2002, p. 1; http://www.flash.net/–apexinsp/eddy.htm.

Web Page entitled "Ultrasonic" by Apex Inspections, Inc., Corporate Member of the American Society for Non–Destructive Testing Since 1999, dated Feb. 15, 2002, p. 1; http://www.flash.net/–apexinsp/ultra.htm.

Web Page entitled "Welcome to Apex Inspections, Inc." by Apex Inspections, Inc., Corporate Member of the American Society for Non–Destructive Testing Since 1999, dated Feb. 15, 2002, pp. 1–3; http://www.flash.net/–apexinsp/home1.htm.

Article entitled "Air Force Steps Up Effort To Take Care For Its Aging Aircraft" by Harold Kennedy; National Defense Magazine, dated Feb. 22, 2002; pp. 1–5; http://www.nationaldefensemagazine.org/article.cfm?Id=704.

Web Page entitled News from the Quality Testing Show; NDT New Horizons on the Pacific, Seattle Bulletins, dated Feb. 22, 2002; http://www.ndt.net/article/report/seattle/q_show.htm.

Web Pate entitled "Ultra Image IV Overview" SAIC, dated Feb. 23, 2002, pp. 1–2; http://www.saic.com/products/inspection/ultra/ultra.html.

Web Page entitled "Ultra Image IV Technical Specification" by SAIC, dated Feb. 23, 2002, pp. 1–3; http://www.saic.com/products/inspection/ultra/ultra–tech.html.

Article entitled "Advanced NDT Instruments" by Orchard House, Orchard Close, NDT—Eddy Current Instrumentation, dated Feb. 23, 2002, pp. 1–3; http://www.advanced–ndt.co.uk/eci.html.

Web Page entitled "Instrumentation for Ultrasonic Nondestructive Testing" by QMI, Inc. dated Feb. 23, 2002, p. 1; http://www.korins.com/m/qmi/PRODUCTS.htm.

Web Page entitled "Air–Coupled Ultrasonic Inspection" by QMI Inc., dated Feb. 23, 2002, pp. 1–3; http://www.korins.com/m/qmi/AIRSCAN.htm.

Web Page entitled "Landings: Aircraft Manufacturers", dated Feb. 23, 2002; pp. 1–7; http://www.landings.com/evird.acgi?pass*43428855!mtd*40!ref*www.../!pg*aircraft–manuf.htm.

Web Page entitled "Technologies We Develop" SAIC, dated Feb. 23, 2002, pp. 1–2; http://www.saic.com./nde/.

Web Page entitled "Intelligent Sensing Technologies, LLC," Stevens Institute of Technology, dated Feb. 23, 2002, pp. 1–2; http://attila.stevens–tech.edu/tvi/ist.htm.

Web Page entitled "CORVIB Precision Measurement Instruments," dated Feb. 23, 2002, pp. 1–2; http://www.corvib.com/.

Web Page entitled Centurion NDT "The Most Recognized Products in NDT," dated Feb. 23, 2002, pp. 1–2, http://www.centurionndt.com/products.htm.

Web page entitled "Mobile Automated Scanner: Moving this 'maus' makes aircraft inspections click", p. 1, dated Feb. 25, 2002; http://www.afmc.wpafb.af.mil/organizations/HQ–AFMC/PA/leading_edge/archives/2000/f . . . .

Web Page entitled "McDonnell Douglas Aerospace–St. Louis (Boeing Aircraft and Missiles) —St. Louis, MO, Best Practice: Automated Ultrasonic Scanning System," dated Feb. 25, 2002, pp. 1–2; http://www.bmpcoe.org/bestpractices/internal/mdasl/mdasl_20.html.

Web Page entitled "Tomographic Acoustic Micro Imaging (TAMI)™ Improves Acoustical Analysis of Flip Chip Packages," Scanning Acoustic Microscopy—Technical Papers consisting of 7 Sections entitled: (1) "TAMI p. 1—Abstract," pp. 1–2; (2) "TAMI p. 2—Background," pp. 1–2; (3) "TAMI p. 3—Conventional Acoustic Analysis and Displays," pp. 1–2; (4) "TAMI p. 4—untitled, " pp. 1–2; (5) "TAMI p. 5—Tomographic Acoustic Micro–Imaging (TAMI)," pp. 1–2; (6) "TAMI p. 6—Flip Chip Analysis Using TAMI Scan," pp. 1–3; (7) "TAMI p. 7—Conclusions," p. 1; http://www.sonix.com/sam/papers/tami1.htm through http://www.sonix.com/sam/papers/tami7.htm.

Article entitled "Catalog 8082/USA Linear Servo Motors and Systems Specifications", by Parker Automation; Parker Hannifin Corporation, Irwin, Pennsylvania, pp. 9–12, C9, 14, 16, and 18.

Article entitled "Catalog 8082/USA Linear Servo Motors and Systems About Linear Motors . . . " by Parker Automation; Parker Hannifin Corporation, Irwin Pennsylvania, pp. 4, 5, 8, C1, C14.

Article entitled "Catalog 8082/USA Linear Servo Motors and Systems 404LXR Series Dimensions (mm)" by Parker Automation; Parker Hannifin Corporation, Irwin Pennsylvania, pp. 14, 16, 18.

Article entitled "Gem6K Drive/Controllers," by Parker Automation; Parker Hannifin Corp., pp. 1–2;.

Article entitled "Mobile Automated Scanner Large Area Rapid Inspection for Disbonds Mobile Automated Scanner (MAUS) IV," p. 1.

Article entitled "SJKB Series DC Elecric, Multi Energy & Internal Combustion Articulating Booms" by SkyJack Incorporated, pp. 1–4.

* cited by examiner

SCANNING ACOUSTIC MICROSCOPY

CROSS-REFERENCE TO RELATED APPLICATION

This application claims priority to U.S. provisional applications entitled: "Scanning Acoustic Microscopy," having Ser. No. 60/355,201, filed Feb. 8, 2002; "Acoustic Coupling," having Ser. No. 60/355,649, filed Feb. 8, 2002; and "Apparatus For Reflection Mode Acoustic Microscopy Scanning Of An Object," having Ser. No. 60/378,450 filed May 7, 2002, all of which are entirely incorporated herein by reference. This application is one of five co-pending, commonly assigned U.S. Patent Applications all of which have the same filing date of May 31, 2002. The other co-pending Applications are entitled "Flowing Fluid Acoustic Coupling," Ser. No. 10/159,585; "Acoustic Coupling With A Fluid Bath," Ser. No. 10/159,441; "Acoustic Coupling With A Fluid Bath," Ser. No. 10/160,493; and "Non-Fluid Acoustic Coupling," Ser. No. 10/191,044, and all of the above-mentioned co-pending applications are hereby incorporated into this document by reference.

TECHNICAL FIELD

The present invention is generally related to the examining of the internal structure of materials and, more particularly, is related to a system and method for the non-destructive internal examination of a material.

BACKGROUND OF THE INVENTION

If a structure, such as a machine or a part of a product, has a defect, such as a crack, a void, or a recess, there is a risk that the machine or part will become inoperable due to the defect. Thus, it is desired that the part having such a defect is eliminated or replaced by detecting the presence of such a defect in advance of the machine or part becoming inoperable. For example, aircraft skins and other manufactured components are frequently made from laminates, which are layers of material adhered together by layers of adhesive, such as, but not limited to, sealant, epoxy, and glue, interposing the layers of material. Laminates can delaminate when the adhesive layers can no longer adhere the layers of material together. Typically, delamination does not occur spontaneously, but rather, it occurs after voids have formed in the adhesive layers. In addition to concerns about delamination due to voids, laminates can also fail due to cracks. Thus, it is desirable to examine by non-destructive means the internal structure of a laminate to search for voids, cracks, and other internal defects before the laminate fails.

It is desirable that the examination of an object occurs in situ. In situ examination of a component can typically be done more rapidly and inexpensively than non-in situ because there it requires less disassembly and reassembly of the system. It is also desirable that the apparatus used for examining the component be readily transportable.

Thus, a heretofore-unaddressed need exists in the industry to address the aforementioned deficiencies and inadequacies.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
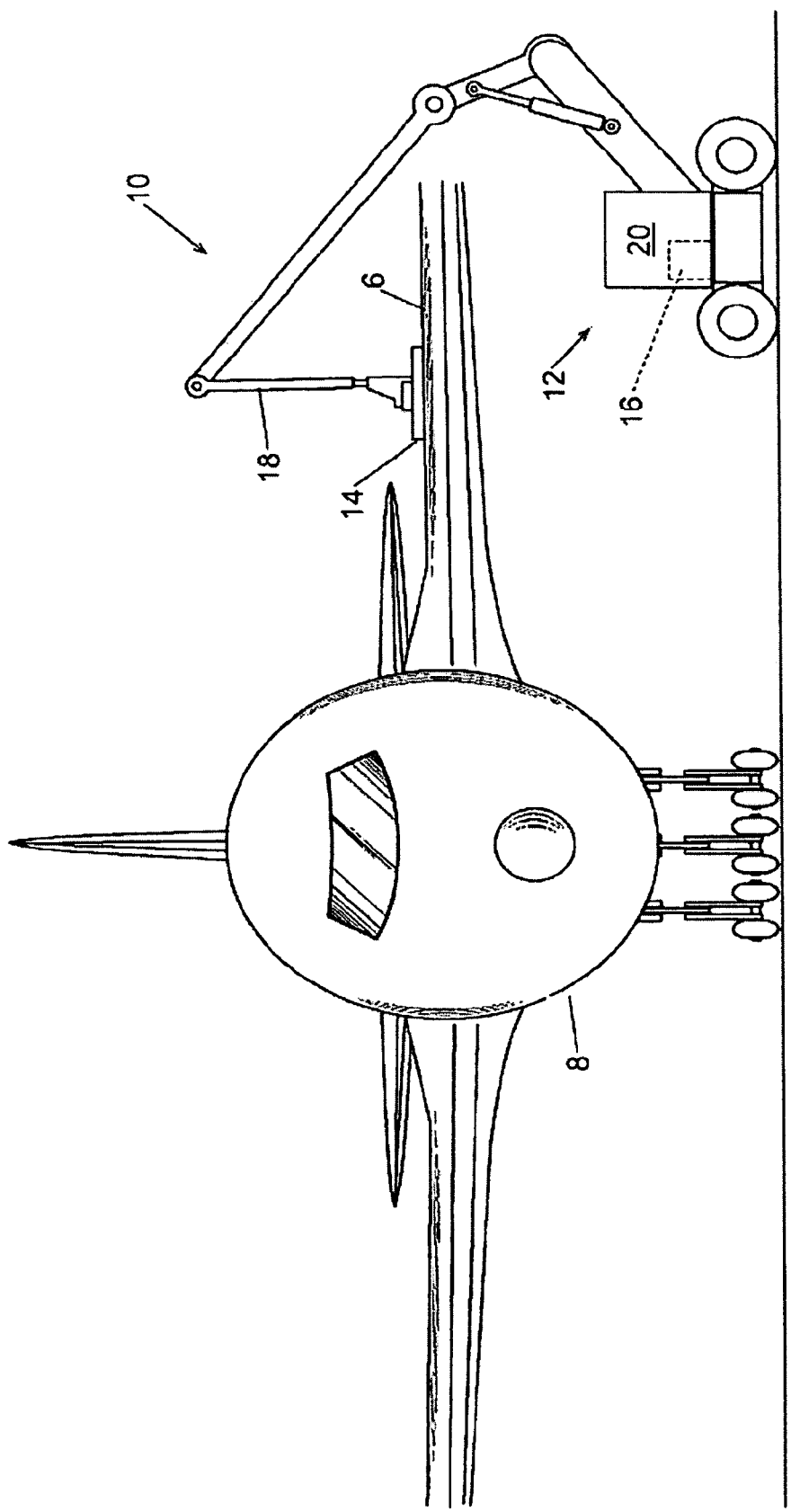
FIG. 1 is a perspective view of a moveable acoustic scanning system scanning a section of an aircraft.

Referring to FIG. 1, a moveable acoustic scanning system (MASS) 10 is used to scan the skin 6 of an aircraft 8. The MASS 10 includes an acoustic scanning assembly (ASA) 14 attached to a positioning apparatus 12. The positioning apparatus 12 includes a base 20 and an extendable arm 18 that extends from base 20. The positioning apparatus includes a control system 16, which is typically a computer, or the like, that is used for, among other things, controlling arm 18. In one preferred embodiment, the base 20 is moveable so that the arm 18 can be readily moved around the aircraft 8 and positioned near subsequent aircraft. Non-limiting examples of a moveable base include but are not limited to trucks, trolleys, carts, scissor-jack, sky-jacks, and hand cars. With the arm 18 positioned proximal to the aircraft 8, the arm 18 is used to position the ASA 14 proximal to selected portions of the aircraft 8. In one preferred embodiment, the arm 18 is adapted to move in three-dimensions so that the ASA 14 can be positioned against the aircraft 8 in orientations ranging from horizontal to vertical. In one preferred embodiment, the arm 18 includes a mechanism such as, but not limited to, hydraulically actuated jaws or clamps (not shown) that grip the ASA 14. After the ASA 14 is attached to the skin 6 of the aircraft 8, the control system 16 releases the ASA 14 so that they are not rigidly coupled together during a scan. The arm 18 releases the ASA 14 so that vibrations are not transmitted from the arm 18 to the ASA 14. In another embodiment, the ASA 14 is manually positioned against selected portions of the aircraft 8.

In one preferred embodiment, the ASA 14 is used to scan a section of the aircraft 8, and when the scan of that section is completed, the controller 16 repositions the ASA 14 to a new section of the aircraft 8. In this manner, the entire skin 6 of the aircraft 8 may be scanned, or selected sections of the aircraft are scanned. The ASA 14 is adapted to scan sections of the aircraft 8 that range in size of up to approximately one meter in length and up to approximately one meter in width.

The ASA 14 can be used to scan a portion of the aircraft 8 that is larger than one meter in length by simply scanning that portion of the aircraft 8 in segments. In other embodiments, the ASA 14 is adapted to scan sections that are either longer or wider or both than one meter.

Typically, the ASA 14 is positioned on the aircraft 8 by the controller 16 manipulating the arm 18. However, in one embodiment, the operator manually controls the arm 18 using controls (not shown) for positioning the ASA 14 against the aircraft 8. Typically, the ASA 14 is positioned against the aircraft 8 within a tolerance of a couple of inches from the desired location, and the ASA 14 can resolve features in the 1 to 200 micron range. A relatively precise determination of the location of the ASA 14 is determined by comparing the scanned structural features such as rivets with their known locations. Thus, although it is preferable to position the ASA 14 as close as possible to a desired location so as to reduce the amount of unnecessary scanning, it is not necessary to place it in an exact location because a precise position of the ASA 14 is determined from the scanning results. Therefore, it is not necessary for the operator to spend an inordinate amount of time positioning the ASA 14 to an exact location.

Acoustic Scanning Assembly

Figure 2A:
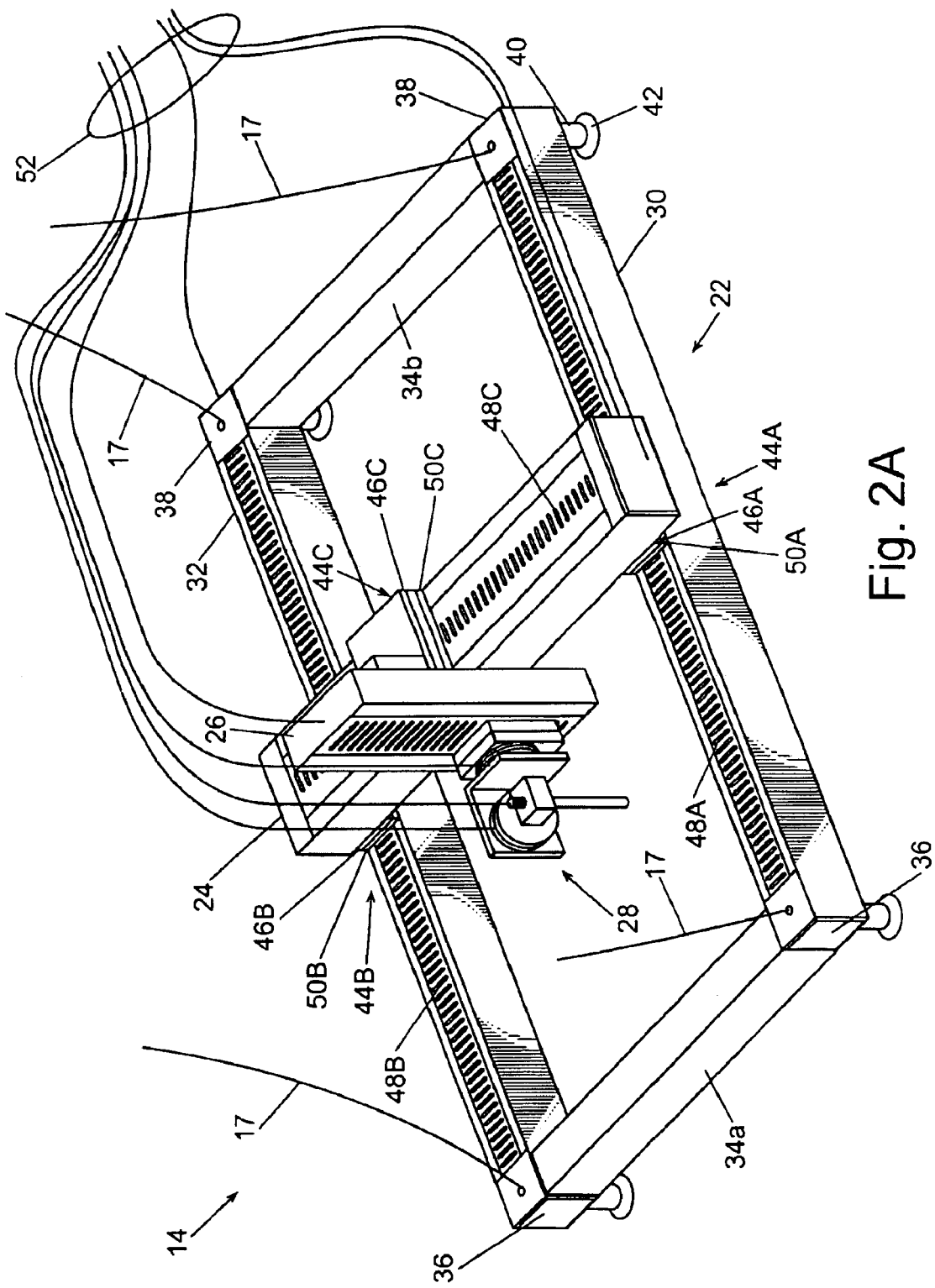
FIG. 2A is a perspective view of an acoustic scanning apparatus attached to a section of an aircraft.
Figure 2B:
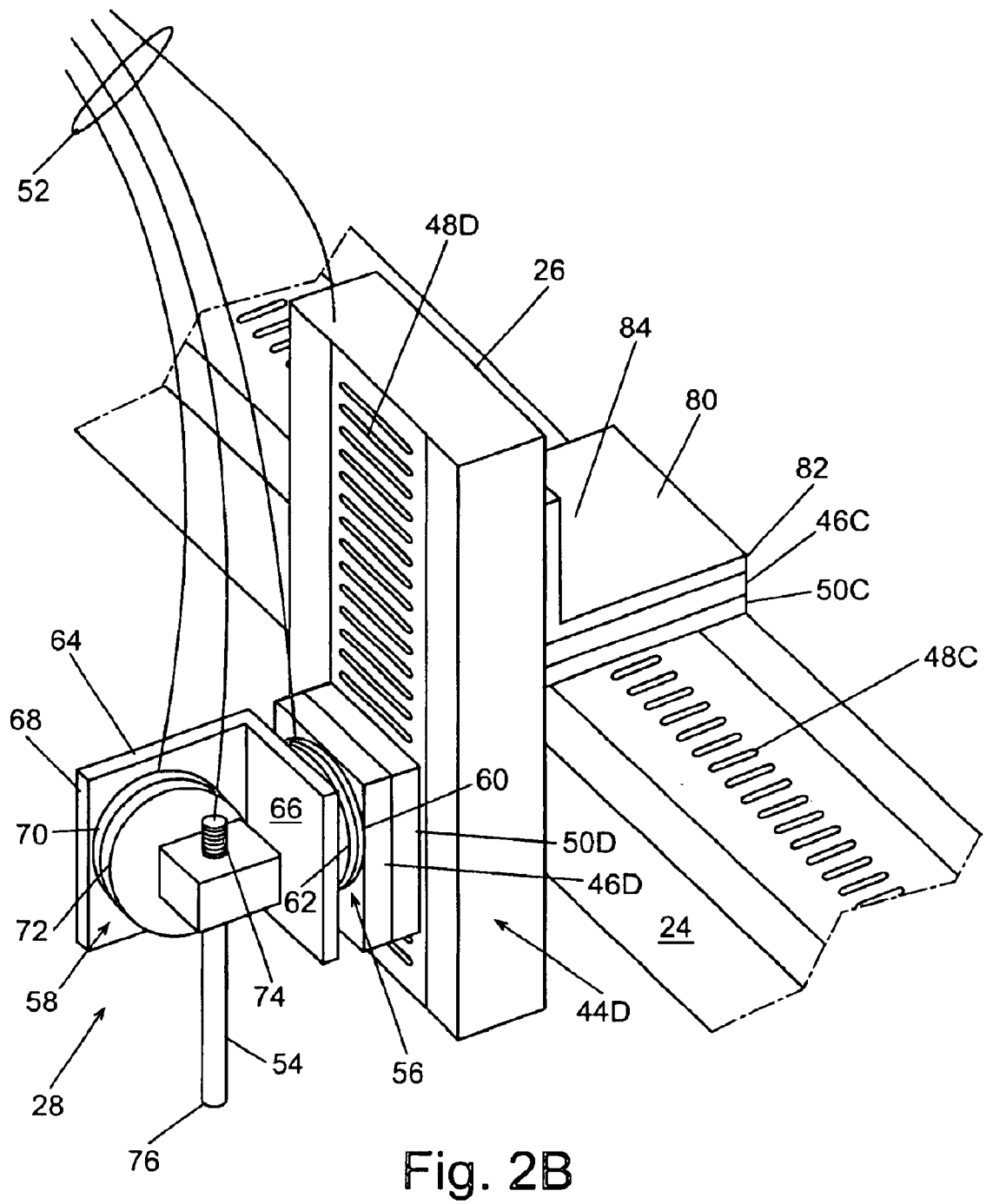
FIG. 2B is a perspective view of an acoustic transducer pivoting assembly.

Referring now to FIG. 2, the ASA 14 includes a base-frame 22, a moveable platform 24, and an acoustic transducer pivoting assembly 28. The base-frame 22 includes a pair of aligned support platforms 30 and 32 and a pair of cross-members 34. The support platforms 30 and 32 each have opposed front and rear ends 36 and 38, respectively. The cross-member 34A is coupled to the front end 36 of the support platform 30 and extends to the front end of the support platform 32 and is coupled thereto. Similarly, the cross-member 34B is coupled to the rear end 38 of each support platform 30 and 32 and extends therebetween.

In one preferred embodiment, the ASA 14 is suspended from arm 18 by support cables 17, which are coupled to the cross members 34. The controller 16 positions the ASA 14 above a desired section of the aircraft, and then lowers the ASA 14 onto the desired sections. The ASA 14 can be raised or lowered by either moving the arm 18 upward or downward or by reeling the support cables 17 in or out. Either way, with the ASA 14 positioned on the skin 6, slack is introduced into the cables 17, so that vibrations are not transferred between the arm 18 and ASA 14.

In one preferred embodiment, the support platform 30 and 32 and the cross members 34 define a rigid structure having a closed perimeter and an open interior. The open interior extends between the support platforms 30 and 32 from the cross member 34A to the cross member 34B. A projection of the open interior onto the skin 6 represents a maximum scan area, i.e., the area of the skin 6 that is scanned when the base-frame 22 is attached to the skin 6. In some situations, the desired scan area is less than the scan area defined by the base-frame 22.

The base-frame 22 further includes legs 40 that extend from the base frame 22 outward. Each of the legs 40 includes a suction cup 42 that is pressed onto the skin 6 of aircraft 8 to hold the base frame 22 in place during a scan. In one preferred embodiment, when the suction cups 42 are pressed against the skin 6, the footprint of each suction cup 42 does not extend into the scanned area. In the preferred embodiment, the suction cup 42 is adapted for remote actuation so that when the suction cup 42 contacts the skin 6, the suction cup is activated by a vacuum or a piezoelectric motor to adhere to the skin 6.

Extending between the support platforms 30 and 32 is the moveable platform 24, which is coupled to the support platforms 30 and 32 such that the moveable platform 24 can slide between the front end 36 and rear end 38 of each support platform 30 and 32 respectively.

In one preferred embodiment, each of the support platforms 30 and 32 and the moveable platform 24 include a linear motor 44 and a table 46. Linear motors are well known to those skilled in the art and will not be discussed in detail. However, a linear motor 44 includes a magnetic strip 48 and a forcer 50 that slides along the magnetic strip 48 responsive to generated electromagnetic fields. Electromagnetic fields are used to both move the forcer 50 and to hold the forcer 50 stationary. Each one of the tables 46 is attached to a single forcer 50. The table 46 moves in conjunction with the forcer 50. In one preferred embodiment, each table 46 defines a generally flat surface having a plurality of mounting holes (not shown), which can be threaded, formed therein. For each table 46, the mounting holes of are adapted to receive fasteners such as, but not limited to screws, bolts and other fasteners known to those skilled in the art so that objects can be attached thereto. In one preferred embodiment, each table 46 and forcer 50 of a linear motor 44 is integrated into a single unit.

The controller 16 is in communication with each of the linear motors 44 via cables 52, which are typically electrical wires or bundles of electrical wires. The cables 52 are used for providing electrical power to the linear motors 44 and for providing a communication link between the controller 16 and the linear motors 44 for, among other thing, communicating positioning information.

Those skilled in the art will recognize that linear motors 44 are merely one mechanism for slidably coupling the elements of the jig together and that other mechanisms including but not limited to jackscrews, worm gears, rack and pinion assemblies, and piezoelectric motion control can be used and are intended to be within the scope of the invention. Typically such mechanisms includes a table or a mounting element that controllably slides along the mechanism by some sort of driving force, such as for example, the rotation of a jackscrew. Thus, the use of linear motors 44 in the ASA 14 is a matter of design choice and is a non-limiting example.

In one preferred embodiment, the moveable platform 24 is removably attached to the tables 46A and 46B by fasteners such as screws or bolts (not shown). However, in an alternative embodiment, the moveable platform 24 is affixed to the tables 46A and 46B by welding or bonding. Those skilled in the art will recognize that welding or bonding are only two methods of affixing and are used here as non-limiting examples methods to affix two or more objects.

In one preferred embodiment, the magnetic strips 48A and 48B of the linear motors 44A and 44B, respectively, extend between the front end 36 and rear end 38 of the support platforms 30 and 32, respectively. Thus, the forcers 48A and 48B with tables 46A and 46B attached thereto, respectively, can traverse between the front end 36 and rear end 38 in a longitudinal direction that is defined by the support platform 30.

The moveable platform 24 extends between the aligned support platforms 30 and 32 and is attached to the tables 46A and 46B of each support platform 30 and 32. Thus, the moveable platform 24 can be longitudinally positioned anywhere along the magnetic strips 48A and 48B, and its position is governed by the controller 16. Initially, the forcers 50A and 50B of the linear motors 44A and 44B are positioned proximal to the front end 36 of the support platforms 30 and 32. The controller 16 provides positioning signals to the linear motors 44A and 44B of the support platforms 30 and 32, respectively, such that the forcers 50A and 50B with tables 46A and 46B attached thereto essentially move in unison and essentially maintain a relative fixed position.

In one preferred embodiment, the moveable platform 24 defines a transverse direction, and the magnetic strip 48C of the moveable platform 24 is of sufficient length such that it extends along the moveable platform 24 between the support platforms 30 and 32. Thus, the transverse position of the forcer 50C with table 46C attached thereto can be positioned by the controller 16 anywhere between the support platforms 30 and 32 along the moveable platform 24.

The acoustic transducer pivoting assembly 28 is attached to the table 46C of the moveable platform 24 by a generally L-shaped mounting platform 80. The mounting platform 80 includes a first arm 82 that is mounted to the table 46C and a second arm 84 that extends approximately perpendicularly from the first arm 82. The first arm 82 is mounted to the table 46C such that the second arm 84 is aligned approximately parallel to the transverse direction defined by the moveable platform 24.

In one preferred embodiment, the first arm 82 is of sufficient length that the second arm 84 overhangs a side of the moveable platform 24. However, in an alternative preferred embodiment, the second arm 84 extends generally upward from the first arm 82, and the first arm 82 is of sufficient length such that the acoustic transducer pivoting assembly 28 can couple to the second arm 84 without touching the moveable platform 24.

In one preferred embodiment, each of the arms 82 and 84 define a plurality of mounting holes (not shown) for receiving fasteners such as, but not limited to, screws and bolts. The mounting platform 80 is removably attached to the table 46C by fasteners (not shown), which extend though the mounting holes in the first arm 82 and couple with the mounting holes defined table 46C. In one preferred embodiment, the first arm 82 is fixedly attached to the table 46C. The mounting holes defined by the second arm 84 are adapted to receive fasteners (not shown) for coupling with the acoustic transducer positioning assembly 28.

Referring to FIG. 2A, the acoustic transducer positioning assembly 28 includes a moveable arm 26, an acoustic transducer assembly 54, and rotary devices 56 and 58. The rotary devices 56 and 58 operate independently so that the acoustic transducer assembly 54 can be rotated about two axes, and the moveable arm is aligned approximately vertically. The moveable arm 26, the rotary devices 56 and 58 are configured to provide a total of 5 degrees of freedom, longitude, transverse, vertical, and two rotational degrees of freedom, pitch and yaw, for the acoustic transducer assembly 54.

In one preferred embodiment, the moveable arm 26 includes a linear motor 44D having a magnetic strip 48D and a forcer 50D with a table 48D attached thereto. The linear motor 44D is merely one mechanism for providing the acoustic transducer assembly 54 with a vertical degree of freedom and that the other mechanisms including but not limited to jackscrews, worm gears, rack and pinion assemblies, and piezoelectric motion control can be used and are intended to be within the scope of the invention.

The moveable arm 26, the rotary devices 56 and 58, and the acoustic transducer assembly 54 are in communication with the controller 16 via cables 52. Commands from the controller 16 and electrical power are supplied to the moveable arm 26 and the rotary devices 56 and 58 through cables 52. The acoustic transducer assembly 54 receives signals from the controller 16, which causes the acoustic transducer assembly 54 to ping the skin surface of the aircraft 8, i.e., to emit an acoustic signal that impinges upon the skin 6. The acoustic transducer assembly 54 sends an echo identical signal to the controller 16. The echo signal corresponds to acoustical signals received by the acoustic transducer assembly 54 that are reflections of the ping.

Rotary devices are well known in the art and shall not be discussed in detail. A non-limiting example of a rotary device is a direct drive rotary table by Parker model no. DM1004.

In one embodiment, the moveable arm 26 is attached to the second arm 82 of the mounting platform 80 by fasteners (not shown) and is aligned such that the moveable arm 26 defines an axis that is approximately perpendicular to both the longitudial direction and the transverse direction. The magnetic strip 48D extends in the direction of the axis along the moveable arm 26. Thus, the forcer 50D with table 46D attached thereto is positionable by the controller 16 in the direction of the axis along the moveable arm 26.

In one preferred embodiment, the rotary device 56 includes opposed mount 60 and table 62. The mount 60 defines a generally flat surface, which is mounted to the table 46D by fasteners such as screws or bolts. The table 62 defines a generally flat mounting surface, which is approximately parallel to the mount 60. The mount 60 and table 62 are pivotally coupled together such that the generally flat mounting surface defined by the table 62 is approximately perpendicular to the axis of rotation, which is called the pitch axis. The table 62 includes a plurality of mounting holes (not shown), which can be threaded and which are adapted to receive fasteners such as, but not limited to, screws or bolts for affixing objects thereto.

An L-shaped mounting plate 64 is mounted to the table 62 by fasteners such as screws or bolts. The L-shaped mounting plate 64 includes a first arm 66, which is attached to the table 62, and a second arm 68, which is aligned approximately perpendicular to the first arm 66. The second arm 68 includes a plurality of mounting holes (not shown) for receiving fasteners such as screws and bolts for affixing objects thereto. The rotary device 58 is attached to the second arm by fasteners and is substantially similar to the rotary device 56.

The rotary device 58 includes a mount 70, which defines a first flat surface, and a table 72, which defines a second flat surface that is substantially parallel to the first flat surface. The mount 70 is attached to the second arm 68 by fasteners and the table 72 is pivotally coupled to the mount 70.

The table 72 includes a plurality of mounting holes (not shown) which can be threaded for receiving fasteners. The table 72 is pivotable amount a yaw axis that is approximately perpendicular to the generally flat surface defined by the table 72. In one embodiment, the acoustic transducer assembly 54 is cylindrical and has a threaded end 74 and an opposed end 76, where acoustic signals are emitted and received.

The threaded end 74 is removably attached to a mounting block 78 by screwing the threaded end 74 into a threaded hole (not shown) formed in mounting block 78. The mounting block 78 is removably attached to table 72 by fasteners such as screws or bolts.

Acoustic signals emitted from the acoustic transducer assembly 54 have a predetermined focal length and by adjusting the position of table 46(d) along moveable arm 26 and adjusting the alignment of the acoustic transducer assembly 54 using rotatable devices 56 and 58 the emitted acoustic signals can be focused above, on, or below the surface of the skin 6 such that the propagation direction of the emitted acoustic signal is normal to the surface or non-normal to the surface.

The controller 16 can move the acoustic transducer pivoting assembly 28 in two dimensions: along the longitudinal direction by moving the forcers 50A and 50B; along the transverse direction by moving the forcer 50C. Furthermore, the controller 16 can move the acoustic transducer assembly 54 along the axis defined by moveable arm 26 by moving the forcer 50D of linear motor 44D and rotate the acoustic transducer assembly about two axes the pitch and yaw axes, using rotatable devices 56 and 58. Because the acoustic transducer assembly 54 has five degrees of freedom, the controller 16 can position the acoustic transducer assembly 54 so as to compensate for the contour of the scanned skin 6 during a scan of the skin 6 of the aircraft 8. In other words, the vertical distance between the acoustic transducer assembly 54 and the skin 6 can be held constant or changed during a scan, regardless of whether the scanned skin 6 is flat or curved or irregular, and the acoustic transducer assembly 54 aligned perpendicular or non-perpendicularly to the skin 6.

Figure 10:
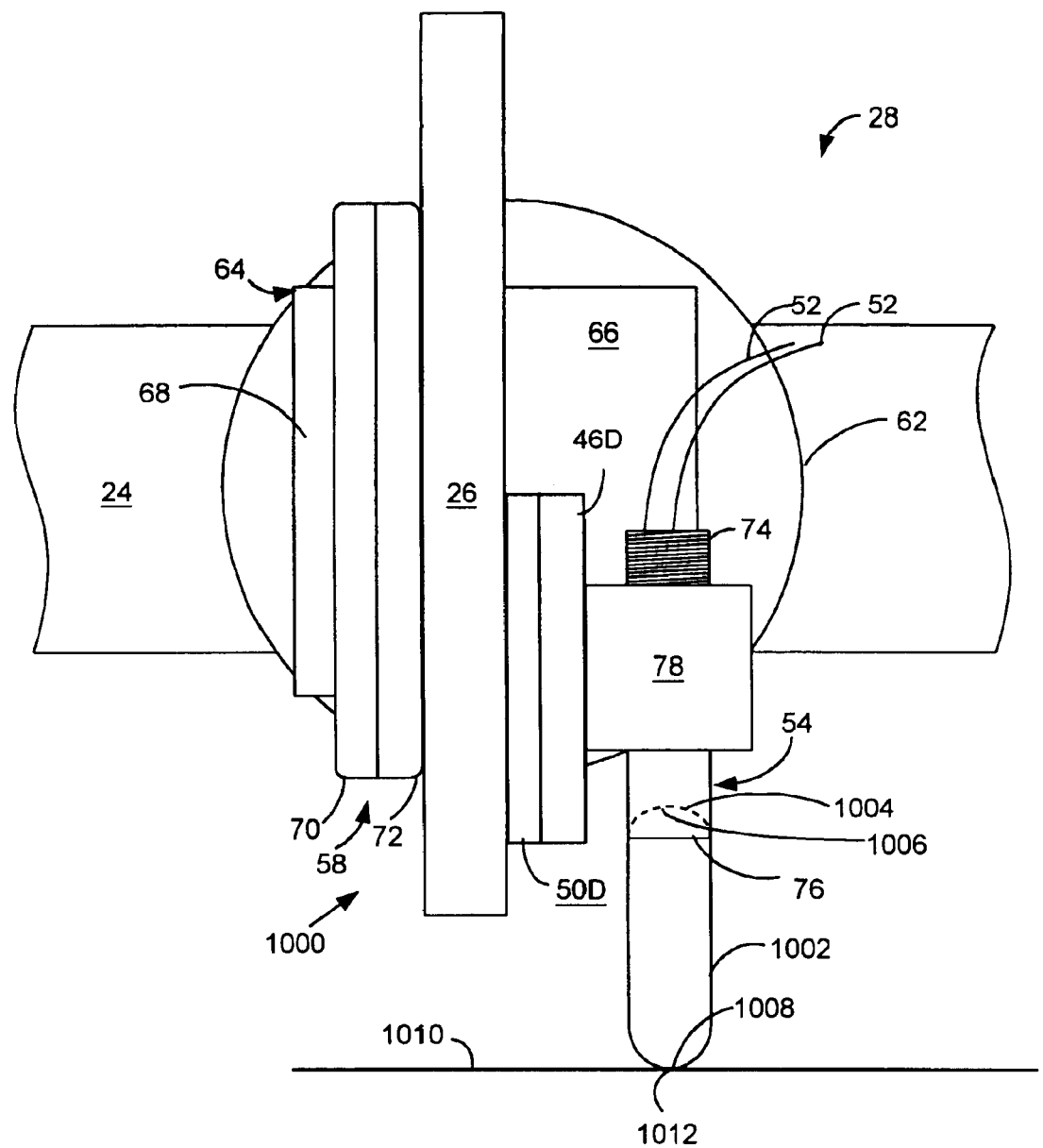
FIG. 10 is a side view of an acoustic transducer pivoting assembly and an acoustic transducer assembly-solid acoustic coupler.

In an alternative embodiment, the elements of the acoustic transducer pivoting assembly 28 is configured in the manner illustrated in FIG. 10. The rotary device 56 is coupled to the mounting platform 80 (not shown), which is coupled to the table 46C (not shown) of the moveable platform 24. The rotary device 56 is aligned approximately vertically, and the L-shaped mounting plate 64 is attached to the table 62 of the rotary device 56. The rotary device 58 is mounted to the second arm 68 of the L-shaped mounting platform 64 in the manner previously described. Attached to the table 72 of the rotary device 58 is the moveable arm 26. Thus, the moveable arm 26 has two degrees of freedom and can be rotated about the pitch axis by rotation of table 56 and about the yaw axis by rotation of table 72. The acoustic transducer assembly 54 is coupled to the table 46D, which is coupled to the forcer 50D, and can be moved along the axis defined by the moveable arm 26. Thus, in this configuration, the acoustic transducer assembly 54 still has five degrees of freedom.

Figure 3:
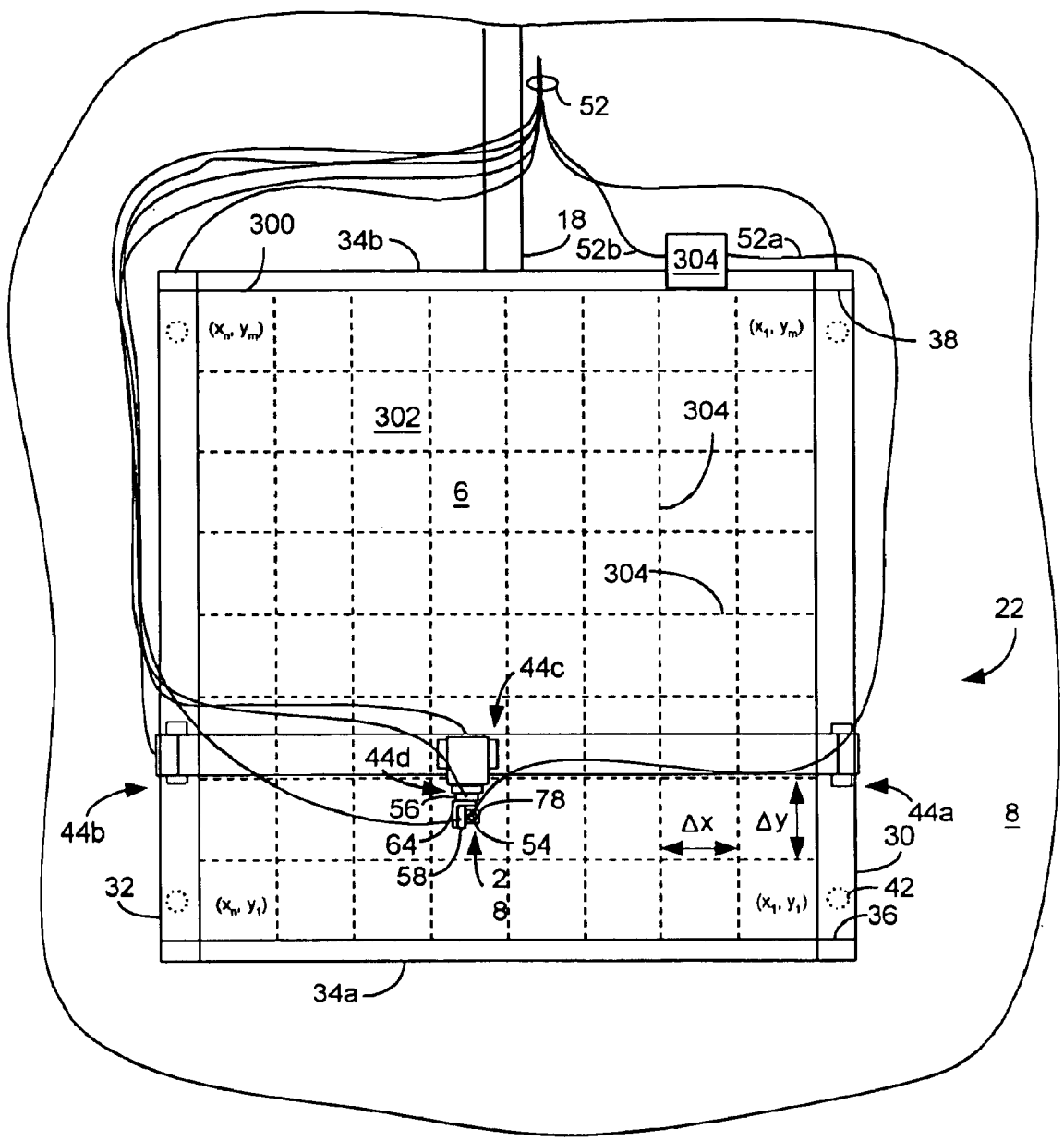
FIG. 3 is top view of an acoustic scanning apparatus attached to a section of an aircraft.

Referring to FIG. 3, in an alternative, the ASA 14 includes a housing 304 that is attached to the cross member 34B. Typically, the housing 304 is water resistant so as to protect internal components and includes an amplifier (not shown): The amplifier is in communication with the controller 16 via cable 52B and with the acoustic transducer assembly 54 via cable 52A. The amplifier receives the echo electrical signal from the acoustic transducer assembly 54 and amplifies it, and transmits the amplified signal to the controller 16 via cable 52B. Amplifying the signal from the acoustic transducer assembly 54 enables the operator to increase the distance between the acoustic transducer assembly 54 and the controller 16 or devices that receive and store or analyze the signal.

In another preferred embodiment, the housing includes a storage device (not shown), the storage device stores the received echo electrical signals from the acoustic transducer assembly 54. The stored echo signals can be download during a scan or at the end of the scan.

Conceptually a scan is performed on the a scan segment 300 of the skin 6 by associating sub-areas 302 of the scan segment 300 with scan points. The dashed lines 304 and the base-frame 22 define each of the sub-areas 302. At the beginning of a scan, the acoustic transducer pivoting assembly 28 is positioned by the controller 16 so that the acoustic transducer assembly 54 is approximately centered on the first scan point labeled $(x_1, y_1)$. The acoustic transducer assembly 54 emits an acoustic signal that pings or impinges on the sub-area 302 associated with the scan point $(x_1, y_1)$.

The acoustic transducer assembly 54 then receives acoustic signals that the are reflections of the emitted acoustic signal. The acoustic transducer assembly 54 converts the reflected acoustic signals into electrical signals, and transmits the electrical signals to the amplifier, which in turn amplifies and transmits the signal to the controller 16.

In response to commands from the controller 16, the acoustic transducer pivoting assembly 28 is moved by an amount of delta x in the transverse direction, and then the acoustic transducer assembly 54 repeats the process of emitting an acoustic signal and receiving reflected acoustic signals. Typically, a transverse scan segment is completed after all of the scan points that have the same longitudinal value, i.e., the same y value, between $x_l$ and $x_m$, inclusive, have been scanned. However, in some situations, the operator may choose to have a transverse scan that is merely a portion of the scan points having the same longitudinal value between the support platforms 30 and 32. In that case, the controller 16 scans the acoustic transducer over the selected scan points.

Once a transverse scan has been completed, the controller 16 translates the forcer 50C with acoustic transducer pivoting assembly 28 coupled thereto such that the acoustic transducer pivoting assembly 28 is repositioned above the first scan point of that transverse run. Next, the controller 16 translates the moveable support platform 24 by an amount delta y by repositioning the forcers 50A and 50B by the amount delta y. The controller 16 then commences with another transverse scan. In this manner, all of the scan points from $(x_1, y_1)$ to $(x_m, y_n)$, inclusive, or a sub-portion of the thereof, are scanned. The transverse distance, delta x, and longitudinal distance, delta y, are predetermined by the operator. Typical, delta x and delta y are in the 20–50 micron range.

Acoustic Scan

Figure 4:
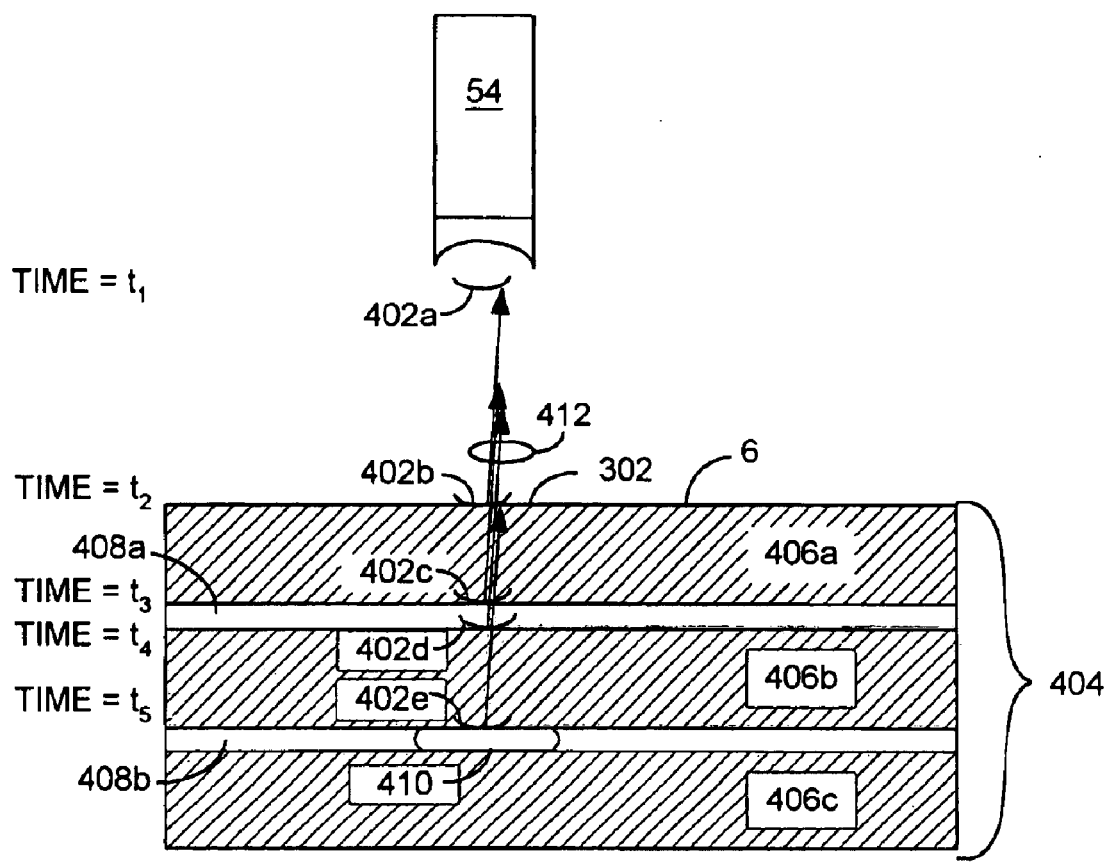
FIG. 4 is diagram of an acoustic transducer assembly emitting an acoustic signal onto a laminate and the reflected acoustic signals.

Referring to FIG. 4, at time $t_1$ the acoustic transducer assembly 54 emits an acoustic signal 402A. The acoustic signal 402B acoustically impinges the surface of sub-area 302 of the skin 6 at time $t_2$. Typically, the signals 402A and 402B are the same, however, in some situations the magnitude of signal 402B is less than the magnitude of signal 402A because a portion of signal 402A is reflected, scattered, or absorbed before it impinges upon the surface of the sub-area 302. The acoustic signals 402B, 402C, 402D, and 402E are all at least a portion of the emitted acoustic signal 402A. They are designated differently to denote changes in their magnitudes due to reflections and absorption.

The skin 6 is a laminate 404 made up of multiple layers of at least one material 406 and adhesive layers 408. Acoustic signals are partially reflected at the interface of any discontinuity in the acoustic impedance of the medium through which the acoustic signal is traveling. Discontinuities can be caused by, among other things, stresses within the material or by changes in density, which typically occur at the interface of the adhesive layer 408 and the material layer 406 and at the surface of the skin 6. Thus, at time $t_2$ a portion of the acoustic signal 402B penetrates the surface of the sub-area 302 and propagates into the laminate 408 and a portion of the signal is reflected backwards towards the acoustic transducer assembly 54, the reflected portion of the signal is the acoustic signal 412.

At time $t_3$, the acoustic signal 402C is incident upon the interface of the adhesive layer 408A and material 406A, where another portion of the emitted signal 402 is reflected. Similarly, at time $t_4$ some of the acoustic signal 402D is reflected at the interface of the adhesive layer 408A and material 406B.

The magnitude of the reflected acoustic signal 412 is related to both the size of the discontinuity and to the magnitude of the change in the acoustic impedance. A void in a material will generally produce such a large change in the acoustic impedance of the material that an acoustic signal will be totally reflected. Thus, at time $t_5$, the acoustic signal 402E is essentially totally reflected by the void 410 in adhesive layer 408B.

It should be remembered that any change in the acoustic impedance of a medium reflects acoustic signal propagating in that medium. Consequently, the acoustic signal 402 will normally be reflected at both the interfaces of different layers of material and within one or more layers of a material. The reflections shown in FIG. 4 are merely illustrative and are not intended to signify all of the reflections that occur within the laminate 404.

Figure 5:
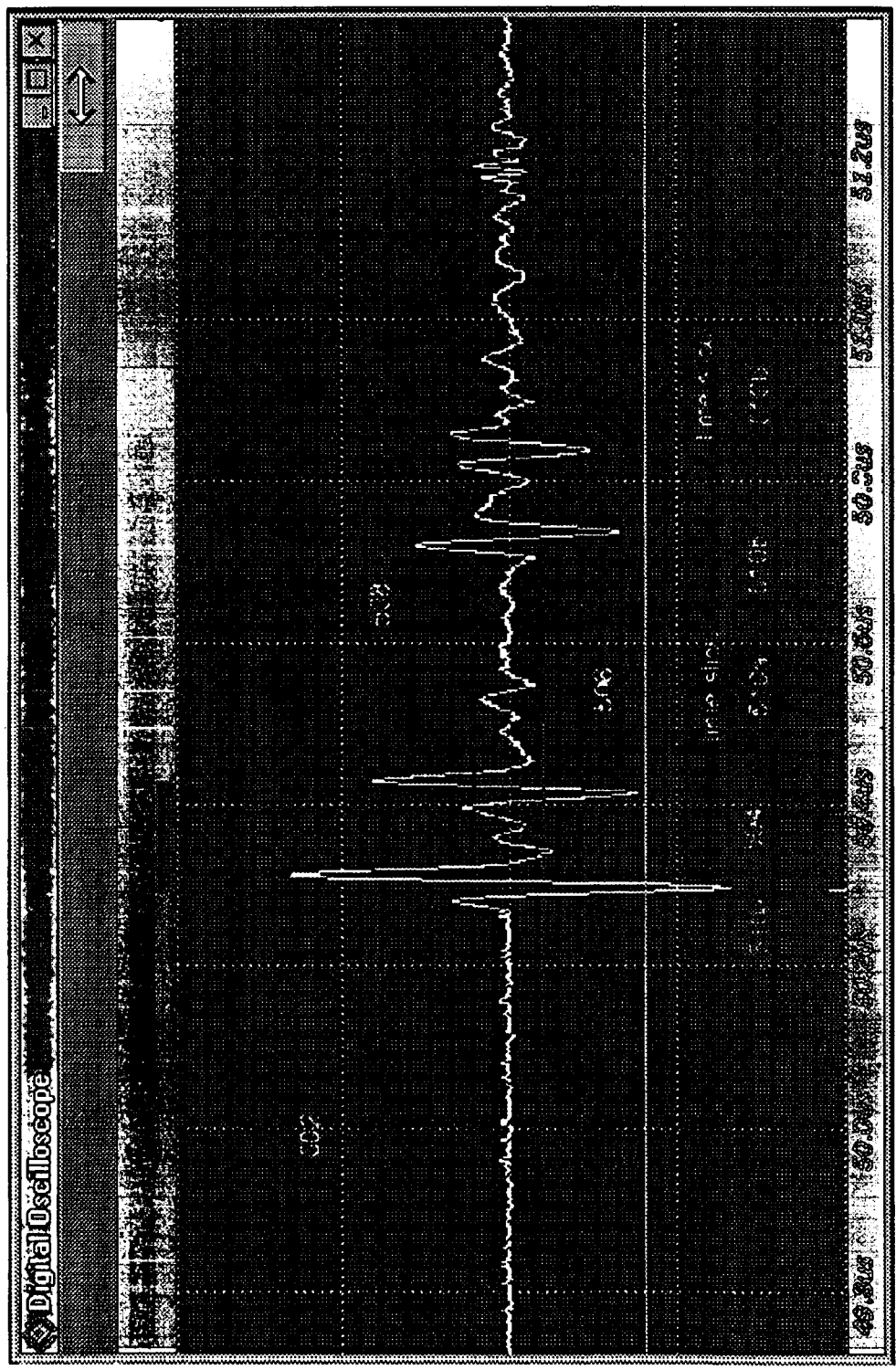
FIG. 5 is a graph of reflected acoustic signals received by an acoustic transducer versus time.

Typically, the acoustic transducer assembly 54 emits a single acoustic signal 402 that is incident on the sub-area 302 and receives a series of reflected acoustic signals 412, where each of the reflected acoustic signals 412 corresponds to a change in the acoustic impedance encountered by the emitted acoustic signal 402. FIG. 5 is a digitized representation of the acoustic signals received by the acoustic transducer assembly 54 versus time and is known as an A-Scan. The digitized acoustic signal 502 is made up of a series of pulses that include pulse 504, pulse 506 and pulse 508.

The pulse 504 is the first pulse received by the acoustic transducer assembly 54 and corresponds to the portion of the emitted acoustic signal that was reflected from the surface of the sub-area 302, i.e., the first discontinuity in the acoustic impedance encountered by the acoustic signal 402. The pulses 506 and 508 occurred later in time than pulse 504, and therefore, they correspond to discontinuities in the acoustic impedance of the laminate 404. Typically, the pulse 504 is used as a reference pulse, and the time lag between the when the acoustic signal 402A was emitted and when the pulse 504 is received is used for, among other things, determining the distance between surface of the sub-area 302 and the acoustic transducer assembly 54. The relative magnitude of the reflected pulse 504 with respect to the emitted signal 402A can also be used for, among other things, determining whether the acoustic transducer assembly 54 is properly aligned with the surface of the sub-area 302.

In one preferred embodiment, the acoustic signal 502 is divided into multiple time slices such as the time slices shown by gates 510A and 510B. In one preferred embodiment, the acoustic signal 502 is divided into approximately thirty time slices, which can overlap, or abut adjacent time slices, or be distinct, and the time slices can also have different widths. Each time slice that occurs after pulse 504 measures acoustic reflections from a layer within the laminate 408. In one preferred embodiment, the time slices are measured relative to pulse 504 rather than from when the acoustic signal 402A was emitted from the acoustic transducer assembly 54. By using the pulse 504 as a reference point, a time slice corresponds to a layer of material at a given depth from the surface of the material. Whereas, when the time slice is measured from the time the signal was emitted from the acoustic transducer, a time slice corresponds to a layer at a given distance from the acoustic transducer. Therefore, using the pulse 504 as the reference point, one can scan the acoustic transducer assembly 54 across the surface of the skin 6 at different heights from the surface and still measure the acoustic characteristics for a layer at constant depth from the surface.

Figure 6:
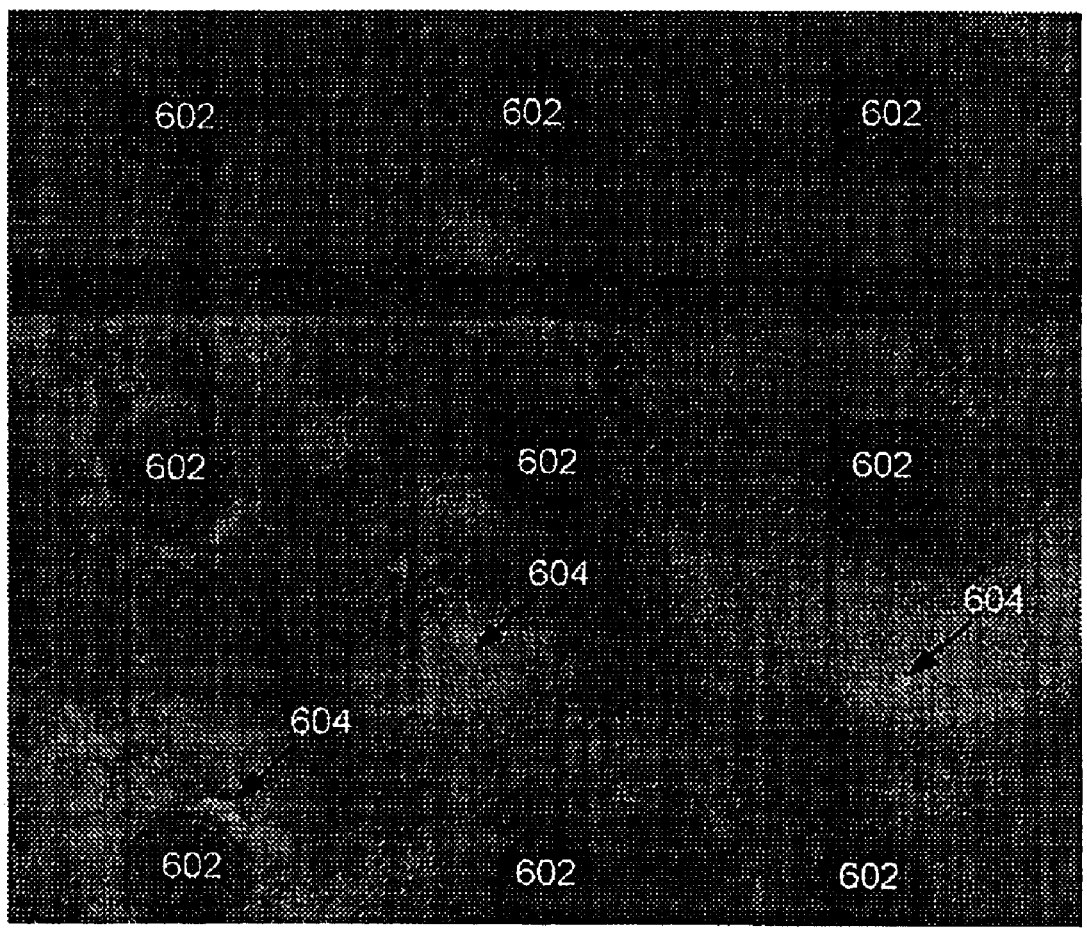
FIG. 6 is a two dimensional image of the internal structure of a layer of an object.

In FIG. 6 an image of a layer of a scanned laminate is shown, and the image is known as a C-Scan In this image the scan points are approximately 20–50 microns apart, and each point of the image corresponds to a digitized representation of the amplitude of a reflected acoustic signal 502 within a predetermined time slice 510. The dark regions represent regions where the amplitude of the reflected signal was low and the light regions represent larger amplitudes of the reflected signal. The points labeled 602 are rivets that extend through the laminate. The points labeled 604 are voids in the adhesive layer.

Controller

Figure 7:
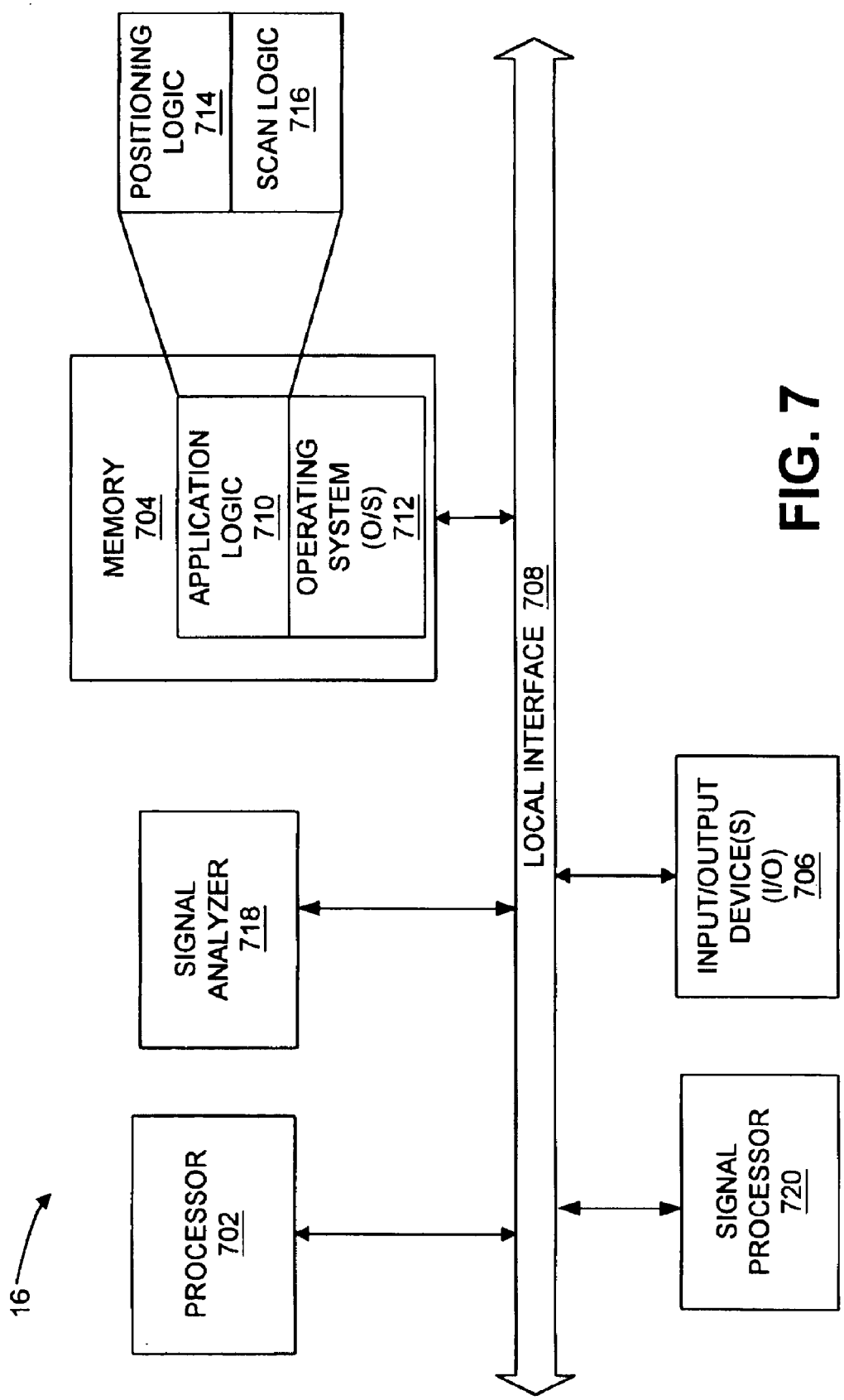
FIG. 7 is block diagram of a computer.
Figure 8:
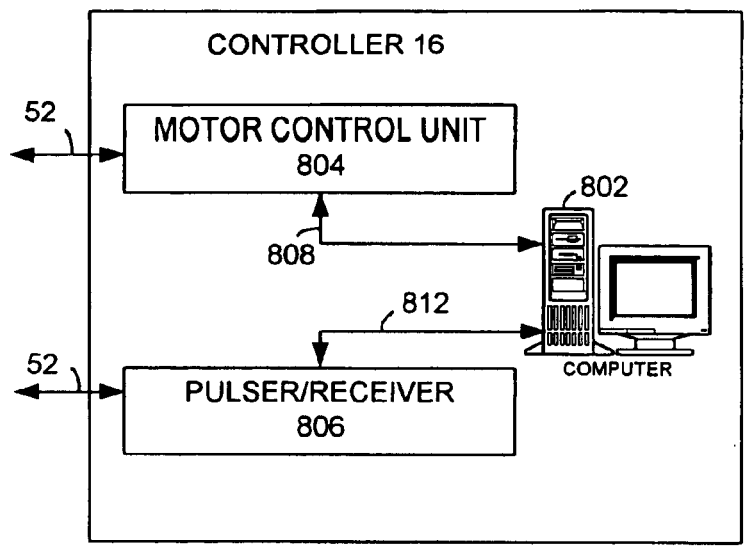
FIG. 8 is a block diagram of a controller.

Referring to FIG. 7, in one preferred embodiment, the controller 16 is a general purpose digital computer, such as a personal computer (PC; IBM-compatible, Apple-compatible, or otherwise), workstation, minicomputer, or mainframe computer. Generally, in terms of hardware architecture, as shown in FIG. 8, the computer 16 includes a processor 702, memory 704, one or more input and/or output (I/O) devices 706 (or peripherals) that are communicatively coupled via a local interface 708, and a signal analyzer 718 that receives the reflected acoustic signals 502 from the acoustic transducer assembly 54 for each scan point. The local interface 708 can be, for example but not limited to, one or more buses or other wired or wireless connections, as is known in the art. The local interface 708 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 702 is a hardware device for executing software, particularly that stored in memory 704. The processor 702 can be any custom made or commercially available processor, a central processing unit (CPU), an auxiliary processor among several processors associated with the computer 16, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68xxx series microprocessor from Motorola Corporation.

The memory 704 can include any one or combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory 704 may incorporate electronic, magnetic, optical, and/or other types of storage media such as R-CD and R-DVD. Note that the memory 704 can have a distributed architecture, where various components are situated remote from one another, but can be accessed by the processor 702.

Information relating to the reflected acoustic signal 412 is stored in memory 704. The related information includes reflected acoustic signal 412 such as the digitized acoustic signal 502 and a position indicator that associates the acoustic signal 502 with a scan point. Frequently, the digitized acoustic signal 502 is stored for only selected scan points instead of for every scan point. The related information also includes digitized times slices that are associated with scan points, which are used for, among other things, generating images of layers such as the image of FIG. 6. The related information can also include transforms of temporal or spatial data associated with acoustic signals 502. For example, the acoustic signal 502 is temporal function that can be transformed into a frequency spectrum by a Fourier-Transform, and in that case, the frequency spectrum is stored in memory 704.

The software in memory 704 may include one or more separate programs, each of which comprises an ordered listing of executable instructions for implementing logical functions. In the example of FIG. 7, the software in the memory 704 includes the Application logic 710 in accordance with the present invention and a suitable operating system (O/S) 712. A non-exhaustive list of examples of suitable commercially available operating systems 712 is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal data assistants (PDAs) (e.g., PalmOS available from Palm Computing, Inc., and Windows CE available from Microsoft Corporation). The operating system 712 essentially controls the execution of other computer programs, such as the Application logic 710, and provides scheduling, input-output control, file and data management, memory management, and communication control and related services.

The Application logic 710 includes one or more source programs, executable programs (object codes), scripts, or any other entities comprising a set of instructions to be performed. A source program is translated via a compiler, assembler, interpreter, or the like, which may or may not be included within the memory 704, so as to operate properly in connection with the O/S 712. Furthermore, the Application logic 710 can be written as: (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada. In one preferred embodiment, the Application logic 710 includes positioning logic 714 and scan logic 716.

The processor 702 uses the positioning logic 714 to control the position and alignment of the acoustic transducer assembly 54. Specifically, the processor 702 sends positioning/alignment commands to the linear motors 44 of the support platforms 30 and 32, moveable platform 24, moveable arm 26, and the rotational devices 56 and 58. The processor 702 also implements the scan logic 716 to send the acoustic transducer assembly 54 signal commands that cause the acoustic transducer assembly 54 to emit acoustic signals. In one embodiment, the scan logic also include logic for generating a digitized image of a scan area, such as the image shown in FIG. 6, and logic for analyzing data such as, but not limited to, Fourier-Transform logic.

The I/O devices 706 may include input devices, for example but not limited to, a keyboard, mouse, scanner, microphone, etc. Furthermore, the I/O devices 706 may also include output devices, for example but not limited to, a printer, display, etc. Finally, the I/O devices 706 may further include devices that communicate both inputs and outputs, for instance but not limited to, a modulator/demodulator (modem; for accessing another device, system, or network), a radio frequency (RF) or other transceiver, a telephonic interface, a bridge, a router, etc. The I/O devices 706 include devices that are coupled to the linear motors 44A–44D, the rotational devices 56 and 58, and the acoustic transducer assembly 54 via communication cables 52.

If the computer 16 is a PC, workstation, or the like, the software in the memory 704 may further include a basic input output system (BIOS) (omitted for simplicity). The BIOS is a set of essential software routines that initialize and test hardware at startup, start the O/S 712, and support the transfer of data among the hardware devices. The BIOS is stored in ROM so that the BIOS can be executed when the computer 16 is activated.

When the computer 16 is in operation, the processor 702 is configured to execute software stored within the memory 704, to communicate data to and from the memory 704, and to generally control operations of the computer 16 pursuant to the software. It should be noted that the Application logic 710 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The Application logic 710 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note, the computer-readable medium could even be paper or another suitable medium upon which the program is printed. As the program can be electronically captured, via for instance optical scanning of the paper or other medium, then compiled, interpreted or otherwise processed in a suitable manner if necessary, and then stored in a computer memory.

In an alternative embodiment, where the Application logic 710 is implemented in hardware, the Application logic 710 can implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc. In addition, the scope of the present invention includes embodying the functionality of the preferred embodiments of the present invention in logic embodied in hardware or software-configured mediums.

In one embodiment, the positioning logic 714 uses a portion of the acoustic signal 502 for determining the current position and alignment or subsequent positions and alignments of the acoustic transducer assembly 54. For example, using reflected signals 502 from previous scan points, the positioning logic 714 can determine the desired vertical and rotational position of the acoustic transducer assembly 54 at its current scan point. By calculating the rate of change of the vertical position and rotational alignment of the acoustic transducer assembly 54 from previous scan points and predicting the vertical position and rotational alignment of the acoustic transducer assembly 54 at its current position. In another embodiment, the desired vertical and rotational position of the acoustic transducer assembly 54 are determined by using feedback. In this embodiment, the acoustic transducer assembly 54 emits a first acoustic signal and based upon the reflected acoustic signal 502 and the positioning logic 714, the processor 702 determines whether the current vertical position and current rotational position of the acoustic transducer assembly 54 are correct. If the acoustic transducer assembly 54 is not correctly positioned and aligned, the processor 702 sends new positioning/alignment commands and rescans the current point. The processor 702 continues to correct the position and alignment of the acoustic transducer assembly 54 until some or all of the received reflected signal 502 falls within some predetermined parameter range, at which point, the received signal 502 is used for analysis.

In one embodiment, the signal analyzer 718 is hardware configured to analyze signals from the acoustic transducer assembly 54, which are received at the computer via I/O device 706. The signal analyzer 718 is typically an analog-to-digital converter (ADC) that is adapted to have a sample rate that may be in the giga-Hertz range.

In one preferred embodiment, the time slices, which were shown in FIG. 6, are wide enough for the signal analyzer 718 to sample 20 to 30 points within each time slice. The output from the signal analyzer 718 for each time slice is then the magnitude of the largest sample point. In one embodiment, the output also includes the phase of the largest sampled point. The output from each time slice is then stored in memory 704 and is associated with the current longitudinal and transverse position of the acoustic transducer assembly 54.

In one embodiment, the computer 16 also includes a signal processor 820 that is used for, among other things, Fourier-Transforms of the received reflected signal 502. Thus, the received acoustic signal 502 is transformed from a temporal quantity to a frequency spectrum. The frequency spectrum is associated with the current longitudinal and transverse location of the acoustic transducer assembly 54 and stored in memory 704. The signal processor 720 is typically hardware such as an ASIC, FPGA, or DSP.

Those skilled in the art will recognize that implementing the signal analyzer 718 and the signal processor 720 in hardware is a design choice. In alternative embodiments, either the signal analyzer 718 or the signal processor 720 or both of them are implemented in either software or firmware.

In one preferred embodiment, the digitized reflected signals of each time slice and the frequency spectrums of the reflected signals 502 are recorded on a media such as a CD or DVD. The recorded scan becomes a snap shot in time of the internal structure of the scanned area. In the future, another scan can be compared with the current scan to determine how, or whether, the internal structure has changed.

Referring to FIG. 8, in an alternative embodiment, the controller 16 includes a computer 802, a motor control unit (MCU) 804 and a pulser/receiver unit 806. In this embodiment, the computer 802 receives, processes, and stores data, and among other things, synchronizes the movement of the acoustic transducer assembly 54 with the emission of acoustic signals 402. The motor control unit 804 is in communication with the computer 802 via the communication link 808 and with the linear motors 44 of ASA 14 via the cables 52. Motor control units are well known in the art and shall not be described in detail. An example of a motor control unit is a Parker Automation Model GEM6K drive/controller.

In one preferred embodiment, the motor control unit 804 is adapted to receive instructions from the computer 802 and control the position and alignment of the acoustic transducer assembly 54 responsive to the instructions from the computer 802. Then, the motor control unit 804 is adapted to control the position and alignment of the acoustic transducer assembly 54 using timing signals from the computer 802 and surface information stored in the motor control unit 802. Typically, the computer 802 controls the position and alignment of the acoustic transducer assembly 54 during initialization, and thereafter the motor control unit 804 controls the position and alignment of the acoustic transducer assembly 54 in responsive to move commands from the computer 802. When the MCU 804 is controlling the position and alignment of the acoustic transducer assembly 54, the MCU 804 tells the computer 802 the current position of the acoustic transducer assembly 54 after each move.

The pulser/receiver 806 is in communication with the computer 802 via communication link 912 and with the acoustic transducer assembly 54 via cables 52. When the acoustic transducer assembly 54 is properly positioned and aligned, the computer 802 sends a signal to the pulser/receiver 806 via communication link 912. The pulser/receiver 806 generates a high voltage signal that is sent to the acoustic transducer assembly 54 via cable 52, which causes the acoustic transducer assembly 54 to emit an acoustic signal 412. The acoustic transducer assembly 54 sends an electrical signal, or an echo signal that corresponds to the reflected acoustic signal 412 to the pulser/receiver 806 via cable 52. The pulser/receiver 806 then relays the echo signal to the computer 802 via communication link 912.

The computer 802 correlates the position of the acoustic transducer assembly 54 with the received echo signal from the pulser/receiver 806. In this embodiment, the computer 802 synchronizes the MCU 804 and the pulser/receiver 806. The MCU 804 moves the acoustic transducer assembly 54, and the pulser/receiver causes it to ping. After the acoustic transducer assembly 54 is correctly positioned and aligned by the MCU 804, the computer 802 sends a signal to the pulser/receiver 806 that causes the acoustic transducer assembly 54 to ping the aircraft 8 by emitting the acoustic signal 402. The MCU 804 does not reposition or realign the acoustic transducer assembly 54 until the MCU 804 receives a move signal from the computer 802. The computer 802 does not send a move signal to the MCU 804 until after the computer 802 has received the echo signal from the pulser/receiver 806.

Figure 9:
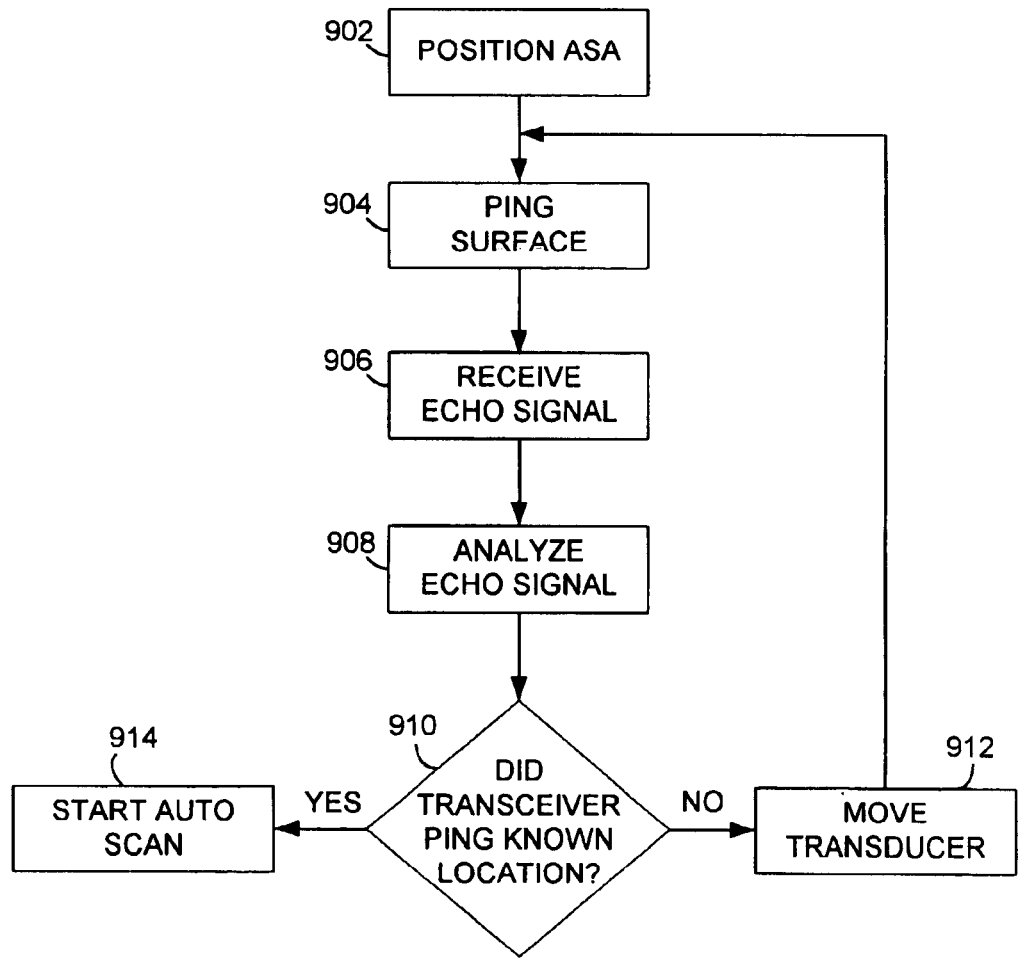
FIG. 9 is a is a flow chart of one example method for scanning a surface.

Referring to FIG. 9, which illustrates one method of initializing the ASA 14, in step 902, the ASA 14 is positioned on the skin 6 at a position that is approximately the desired location of the ASA 14. In step 904, the computer 802 sends a signal to the pulser/receiver 806, which in turn sends a high voltage signal to the acoustic transducer assembly 54 that causes the acoustic transducer assembly 54 to emit the acoustic signal 402, or to "ping" the surface.

In step 906, the acoustic transducer assembly 54 receives the reflected acoustic signal 412 and thereby produces an electrical signal, or the echo signal that corresponds to the reflected acoustic signal 412. The echo signal is sent to the computer 802 via the pulser/receiver 808.

In step 908, the computer 802 analyzes the echo signal. In one embodiment, the echo signal is analyzed to determine the amount of reflection for a time slice that corresponds to the interface of an adhesive-material layer. If the amount of reflection is smaller than a predetermined threshold, then the computer 802 determines that the acoustic impedance at that layer is substantially uniform, which occurs when a rivet extends through the adhesive-material interface.

Next, in step 910, the computer 802 determines if the acoustic transducer assembly 54 pinged a known location. The computer 802 knows the structural features and the contours of the skin 6 of the aircraft and knows how the structural features such as rivets and contours will reflect acoustic signals. If the echo signal did not correspond to a signal reflected from a known location, then the computer proceeds to step 912 and has the motor control unit 804 move the acoustic transducer assembly by an amount that is determined by the computer 802. The computer 802 keeps repeating the steps 904 through 912 until the acoustic transducer assembly 54 has pinged a known location.

After the acoustic transducer assembly 54 is positioned above a known location, the computer 802 proceeds to step 914 and initiates the auto scan mode. In auto-scan mode, the motor control unit 804 uses its knowledge of the contours of the skin 6 to position and align the acoustic transducer assembly 54. In this mode, the computer 802 sends synchronization signals to the motor control unit 804 and pulser/receiver 806, but the computer 802 no longer need determine the position and alignment of the acoustic transducer assembly 54. Typically, the MCU 804 and the computer 802 include storage units (not shown) for storing, among other things, structural information, contour information, etc. about the aircraft 8. This information is typically formatted as a Computer Assisted Design (CAD) file. The MCU 804 uses the CAD file for controlling the position and alignment of the acoustic transducer assembly 54.

Acoustic Coupling

Typically, the acoustic transducer assembly 54 emits an acoustical signal in the 1–200 MHz frequency range. For example, acoustic transducers such as a Sonix series nos. V313 or MSIC, operate in the 1–200 frequency range. A problem associated with operating in this frequency range is that air does not readily transmit acoustic signals in that frequency range because in that frequency range the acoustic impedance of air is so high that acoustic signals are essentially totally reflected. In this section, four different preferred embodiments of devices that enable an operator to perform reflection mode scanning acoustic microscopy of an object such as, but not limited to, the aircraft 8, are described.

Acoustic Transducer Assembly-Solid Acoustic Coupler

In FIG. 10, an acoustic transducer assembly-solid acoustic coupler 1000 is shown mounted to the acoustic transducer pivoting assembly 28. The acoustic transducer assembly-solid acoustic coupler 1000 includes the acoustic transducer assembly 54 and a solid acoustic coupler 1002.

In one preferred embodiment, the solid acoustic coupler 1002 is made from a material such as, but not limited to, epoxy, polyimide, resin, ceramic, metal, polymer, glass, and other materials known to those skilled in the art that can effectively carry acoustic signals in the 1–200 MHz frequency range, or materials that have an acoustic impedance less than air in that frequency range.

The acoustic transducer assembly 54 emits and receives acoustical signals from end 76. Typically, the end 76 is open ended and is formed such that the end includes a bowl shaped face or a concave face 1004 and the acoustic transducer assembly 54 emits and receives acoustical signals through face 1004. Acoustic signals emitted from the acoustic transducer assembly 54 are focused at a predetermined focal length from the end 76, typically in the range of 0.25 inches. The focal length of the acoustic transducer assembly 54 is determined in part by the shape of the face 1004.

The solid acoustic coupler 1002 includes opposed ends 1006 and 1008. The end 1006 is formed such that its shape compliments the shape of face 1004 so that end 1006 and face 1004 fit together with little or no gaps therebetween. The longitudinal length of the solid acoustic coupler 1002, which is the distance between the opposing ends 1006 and 1008, is approximately the focal length of acoustic transducer assembly 54. Thus, emitted acoustic signals from the acoustic transducer assembly 54 are focused at end 1008. However, the longitudinal length of the solid acoustic coupler 1002 is a matter of implementation, and in another alternative embodiment, the longitudinal length of the solid acoustic coupler 1002 is less than the focal length of the acoustic transducer assembly 54. In yet another embodiment, the longitudinal length of the solid acoustic coupler 1002 is greater than the focal length of the acoustic transducer assembly 54.

To scan an object 1010 with the acoustic transducer assembly-solid acoustic coupler 1000, the acoustic transducer pivoting assembly 28 is positioned such that end 1008 makes physical contact with the surface at point 1012. The acoustic transducer assembly 54 emits an acoustic signal, which is carried by the solid acoustic coupler 1002 to the contact point 1012. Through contact point 1012 and end 1008, acoustic signals are passed between the object 1010 and the solid acoustic coupler 1002. Thus, the solid acoustic coupler 1002 carries emitted acoustic signals, which ping contact point 1012, from the acoustic transducer assembly 54. Pinging contact point 1012 generates acoustic signals, which are reflections of the emitted acoustic signals in object 1010. The solid acoustic coupler 1002 carries the reflections to the acoustic transducer assembly 54. After the reflections have been received by the acoustic transducer assembly 54, the controller 16 moves the acoustic transducer pivoting assembly 28 to a new contact point, where the scan process is repeated.

In one embodiment, the acoustic transducer assembly-solid acoustic coupler 1000 is moved between contact points 1012 with the end 1008 being generally in contact with the object 1010 during the movement thereof. In this case, the solid acoustic coupler 1002 is preferably made from a material such as polyimide or other material that will not usually scratch or mar the object 1010.

In another embodiment, when the acoustic transducer pivoting assembly 28 is moved between contact points 1012, the acoustic transducer pivoting assembly 28 is first moved away from the object 1010 so that the end 1008 is not in contact with the object 1010. Then, the acoustic transducer pivoting assembly 28 is moved to a new position and moved closer to the object 1010 until the end 1008 reestablishes contact with the object 1010. In another embodiment, the acoustic transducer pivoting assembly 28 is moved in a saw tooth pattern. In yet another embodiment, one or both of the rotary drives 56 or 58 rotate the acoustic transducer assembly-solid acoustic coupler 1000 such that the end 1008 is not in contact with the object 1010 during movements between contact points 1012. After the acoustic transducer pivoting assembly 28 has been moved to a new position, the acoustic transducer assembly-solid acoustic coupler 1000 is then rotated such that the end 1008 reestablishes contact with object 1010.

In one preferred embodiment, the acoustic transducer assembly 54 and the solid acoustic coupler 1002 are joined together so that there are essentially no gaps between the face 1004 and end 1006. One preferred method for accomplishing this is described hereinbelow. The acoustic transducer assembly 54 is positioned such that the acoustic transducer assembly 54 is substantially vertically aligned with face 1004 pointing upward. A mold (not shown) is removably attached to end 76 extending upwardly therefrom. A predetermined amount of a liquid epoxy or other suitable material known to those skilled in the art is poured into the mold. The liquid flows into the mold and covers the face 1004 of the acoustic transducer assembly 54 and adheres thereto. Typically, the amount of liquid poured into the mold is sufficient to substantially fill the mold. After the liquid has hardened into a solid material, the mold is removed, thereby exposing the solid acoustic coupler 1002. In one embodiment, the end 1008 is substantially shaped by the mold. In another embodiment, the solid acoustic coupler 1002 is processed to form the shape of end 1008.

Acoustic Transducer Assembly Sprayer

Figure 11:
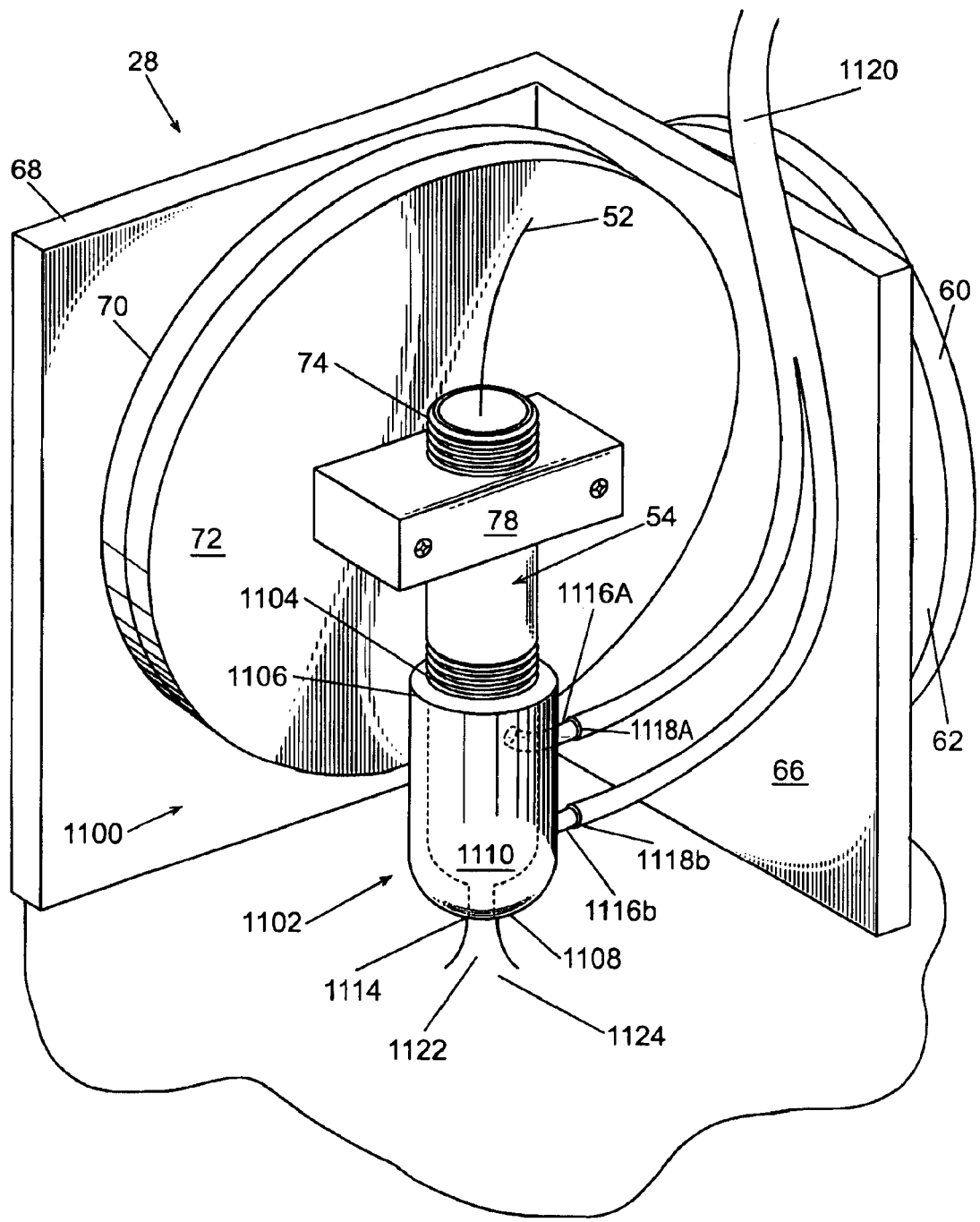
FIG. 11 is perspective view of an acoustical acoustic transducer assembly sprayer.

Referring to FIG. 11, an acoustic transducer assembly sprayer 1100 includes the acoustic transducer assembly 54 and a sprayer 1102. The acoustic transducer assembly 54 includes the opposed threaded ends 74 and threaded end 1104. The threaded end 74 is received by a threaded hole (not shown) formed in the mounting block 78, which is mounted to the table 72 of the rotary device 68.

The sprayer 1102 defines a longitudinal body having opposed ends 1106 and 1108. Extending partially between the opposed ends 1106 and 1108 is a chamber 1110. The end 1106 defines a threaded opening (not shown) that extends from the chamber 1110 to end 1106, and the threaded opening is adapted to mate with the threaded end 1104 of the acoustic transducer assembly 54.

The opposed end 1108 defines a second opening 1114 that is generally aligned with the threaded opening and which is in communication with the chamber 1110. The sprayer 1102 also defines fluid inlet openings 1116a and 1116b, which have spouts 1118a and 1118b inserted therein. The spouts 1118 extend from the chamber 1110 outward beyond the exterior of the sprayer 1102.

Pressurized fluid hoses 1120 are coupled to the spouts 1118 and fluid flows therethrough into the chamber 1110. Hydraulic pressure pushes fluid in the hoses 1120 into the chamber 1110, and consequently, a fluid stream 1122 is expelled from the chamber 1110 by the hydraulic pressure carried by the hoses 1120. The fluid stream 1120 extends outward from end 1108 of the sprayer 1102 and impinges upon the surface 1124. In one preferred embodiment, the fluid stream 1122 is a laminar fluid flow stream.

In one preferred embodiment, the fluid inlet opening 1116a is positioned such that the spout 1118a is approximately aimed at the acoustic transducer assembly 54. In this manner, a stream of fluid carried through tube 1118 flows across the face 1004 of the acoustic transducer assembly 54. Thereby removing any air bubbles from the face.

With the acoustic transducer assembly 54 in communication with the fluid in chamber 1110 and the fluid stream 1122 impinging on the surface 1124, the acoustic transducer assembly 54 is in acoustical communication with the surface 1124. The acoustic impedance of the fluid is such that acoustic signals in the 1–200 MHz frequency range are readily carried. Thus, the acoustic transducer assembly-sprayer 1100 is used to acoustically scan an object such as an aircraft, when the aircraft is disposed in air.

The fluid stream 1122 and the fluid in chamber 1110 communicate acoustic signals between the acoustic transducer assembly 54 and the surface 1124. Thus, a scan is performed by having the acoustic transducer assembly 54 emit an acoustic signal that is carried by the fluid in chamber 1110 and the fluid stream 1122 to the surface 1124. The fluid carries reflections of the emitted acoustic signal back to the acoustic transducer assembly 54. After the acoustic transducer assembly 54 has received the reflection signals, the controller 16 moves the acoustic transducer pivoting assembly 28 to a new position where the process is repeated. In this manner, an object that is substantially disclosed in air can be scanned with the acoustic transducer assembly-sprayer 1100.

Acoustic Transducer Assembly-Fluid Retainer

Figure 12:
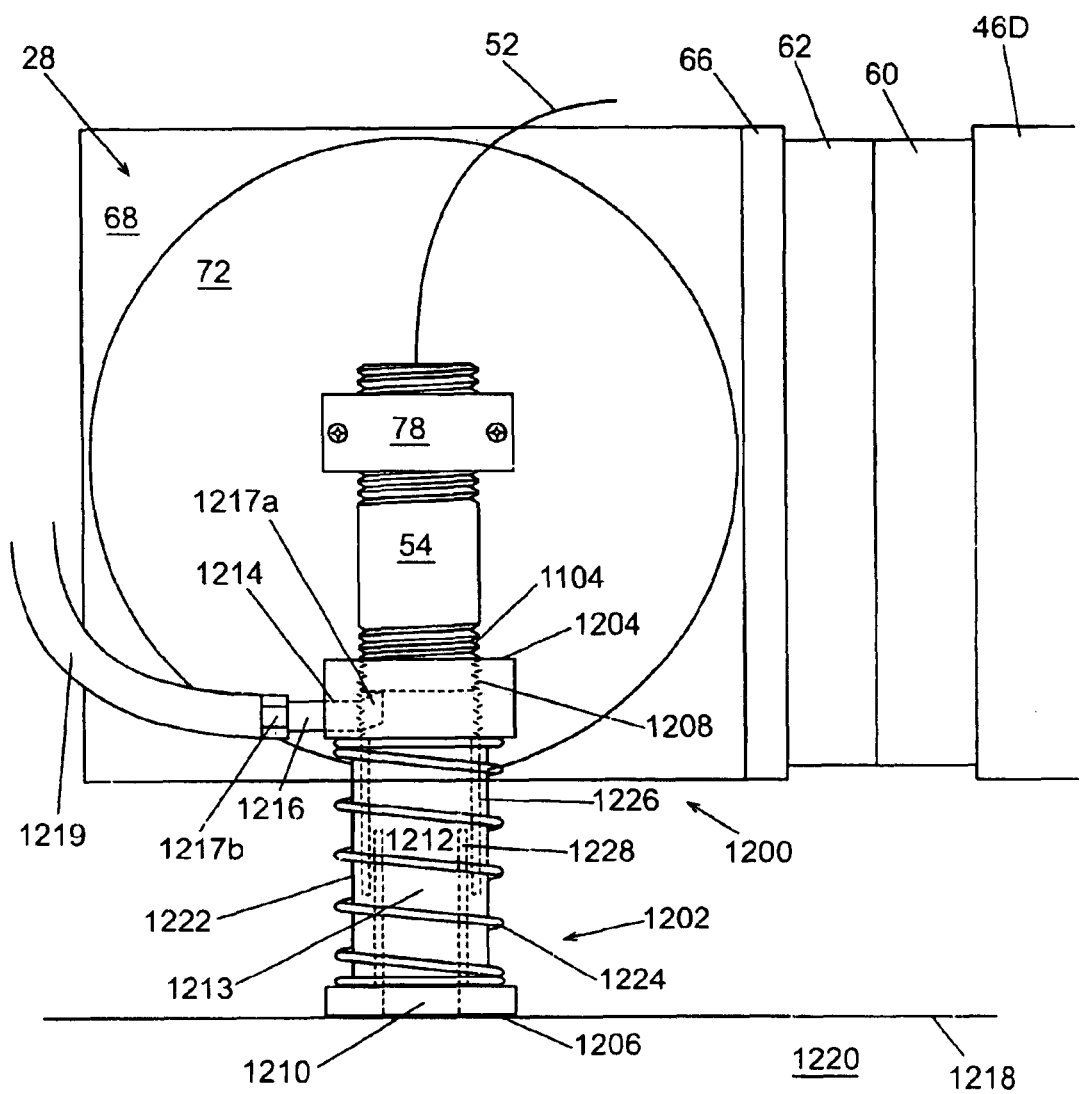
FIG. 12 is a side view of an acoustic transducer assembly-fluid retainer.

Referring to FIG. 12, the acoustic transducer pivoting assembly 28 has an acoustic transducer assembly-fluid retainer 1200 coupled thereto. In this embodiment, the acoustic transducer assembly-fluid retainer 1200 includes the acoustic transducer assembly 54 and a fluid retainer 1202. The acoustic transducer assembly 54 is coupled to the acoustic transducer pivoting assembly 28 via the mounting block 78 in the manner previously described.

The fluid retainer 1202 defines a longitudinal body having opposed ends 1204 and 1206 and the ends 1204 and 1206 each define an opening 1208 and 1210, respectively, which are generally vertically aligned. Typically, the longitudinal length of the fluid retainer 1202 is greater than the focal length of the acoustic transducer assembly 54.

In one preferred embodiment, the opening 1208 is a threaded opening, which is adapted to mate with the threaded end 1104 of acoustic transducer assembly 54. In an alternative embodiment, the acoustic transducer assembly 54 and fluid retainer 1202 are threadably coupled together, but the male-female relationship is reversed so that the fluid retainer 1202 screws into end 76 of the acoustic transducer assembly 54. However, in yet another alternative embodiment, the end 1204 of the fluid retainer 1202 is pressure fit onto end 1104 of the acoustic transducer assembly 54 and held thereon by pressure clamps. In yet another embodiment, the acoustic transducer assembly 54 and fluid retainer 1202 are manufactured as a single non-separable unit.

Extending between opposed ends 1204 and 1206 is a sleeve 1222, which is defines a fluid retaining chamber 1212. The fluid-retaining chamber 1212 is in communication with the openings 1208 and 1210 and contains a fluid 1213 therein. The sleeve 1222 is preferably made from a polymer or other non-rigid material that is essentially impermeable to the fluid 1213. The fluid 1213 carries acoustic signals in the 1 to 200 MHz frequency range.

In one preferred embodiment, the end 1204 defines a fluid inlet opening 1214 that extends approximately horizontally from the opening 1208 thereout, and a spout 1216 having opposed ends 1217a and 1217b. The end 1217a is aimed at the acoustic transducer assembly 54 so that a fluid stream from spout 1216 flows across the face of the acoustic transducer assembly 54. A pressurized fluid hose 1219 is attached to the end 1217b and a fluid flows therethrough into the fluid retainer 1202.

In one preferred embodiment, the end 1204 also defines a relief valve (not shown). When the end 1206 is in contact with the surface 1218, the end 1206 forms an essentially fluid tight seal on the surface 1218. Thus, when fluid flows into the chamber 1212 through fluid inlet tube 1216, air is flushed out of the chamber 1212 through the relief valve.

The end 1206 of the fluid retainer 1202 is annular in shape and is made from an resilient pliable material that conforms to the local contour of a surface 1218 of an object 1220. It is preferable that the end 1206 is made from a material that is essentially impermeable to the fluid in the fluid retaining chamber 1212.

Encompassing the sleeve 1222 is coil spring 1224 that extends between the opposed ends 1204 and 1206. The coil spring 1224 engages the opposed ends 1204 and 1206 and provides a biasing force for pushing the ends 1204 and 1206 apart.

The fluid retainer 1202 also includes a pair of overlapping longitudinal supports 1226 and 1228. The longitudinal support 1226 extends from the end 1204 downward into chamber 1212, and the longitudinal support 1228 extends from end 1206 upward into chamber 1212. The longitudinal support 1226 and 1228 are approximately cylindrical in shape with the longitudinal support 1228 having an outer diameter that is smaller than the inner diameter of the longitudinal support 1226. Thus, the longitudinal support 1226 overlaps the longitudinal support 1228 with the longitudinal support 1228 telescoping within the longitudinal support 1226. The longitudinal support 1226 and 1228 are preferably made from metal or some other rigid material.

In operation, the acoustic pivoting assembly 28 with the acoustic transducer assembly-fluid retainer 1200 attached thereto is positioned such that the end 1206 is in contact with the surface 1218. Preferably, the acoustic transducer assembly 54 is brought close enough to the surface 1218 such that the sleeve 1222 is compressed between ends 1204 and 1206. In that case, the coil spring 1224 provides a biasing force that pushes the end 1206 against the surface 1218. Typically, the end 1206 is pressed against the surface 1218 with sufficient force that it conforms to the local contour of the surface 1218 so as to form an essentially fluid tight seal thereat. However, in one embodiment, the fluid 1213 in the fluid chamber 1212 is under positive pressure from the pressurized fluid hose 1219 so as to prevent air from seeping into the fluid chamber 1212. In that case, some fluid 1213 may seep between the end 1206 and the surface 1218.

The ends 1204 and 1206, the overlapping longitudinal supports 1226 and 1228, and the fluid chamber 1212 are aligned so that the acoustic transducer assembly 54 is in acoustic communication with the surface 1218 via the fluid 1213. The sleeve 1222, the longitudinal supports 1226 and 1228, and the coil spring 1224 cooperate such that the face of the acoustic transducer assembly 54 can be positioned at a distance from the surface 1218 ranging from greater than the focal length of the acoustic transducer assembly 54 to less than the focal length of the acoustic transducer assembly 54. The distance between the face of the acoustic transducer assembly 54 and the surface 1218 can be determined by the controller 16 using the time lag between pinging the surface 1218 and receiving a reflection signal or by using knowledge of the contour of the surface 1218 and knowing the position of the acoustic transducer assembly 54.

The longitudinal supports 1226 and 1228 provide longitudinal support to the sleeve 1222 as the acoustic transducer assembly-fluid retainer 1200 is scanned over the surface 1218. When the acoustic transducer assembly 54 is moved parallel to the surface 1218, the longitudinal support 1226 moves with the acoustic transducer assembly 54 because it and the end 1204 are made from rigid materials. As the longitudinal support 1226 moves parallel to the surface 1218, it engages the longitudinal support 1228 and pushes it in the same direction. The end 1206 moves parallel to the surface 1218 with the movement of the longitudinal support 1228. Thus, the longitudinal alignment of the food retainer 1202 is essentially maintained as the fluid retainer 1202 is moved across the surface 1218 even though the sleeve 1222 is pliable and the end 1206 is forming an essentially fluid tight seal on the surface 1218.

Fluid Bath Acoustic Coupler

Figure 13:
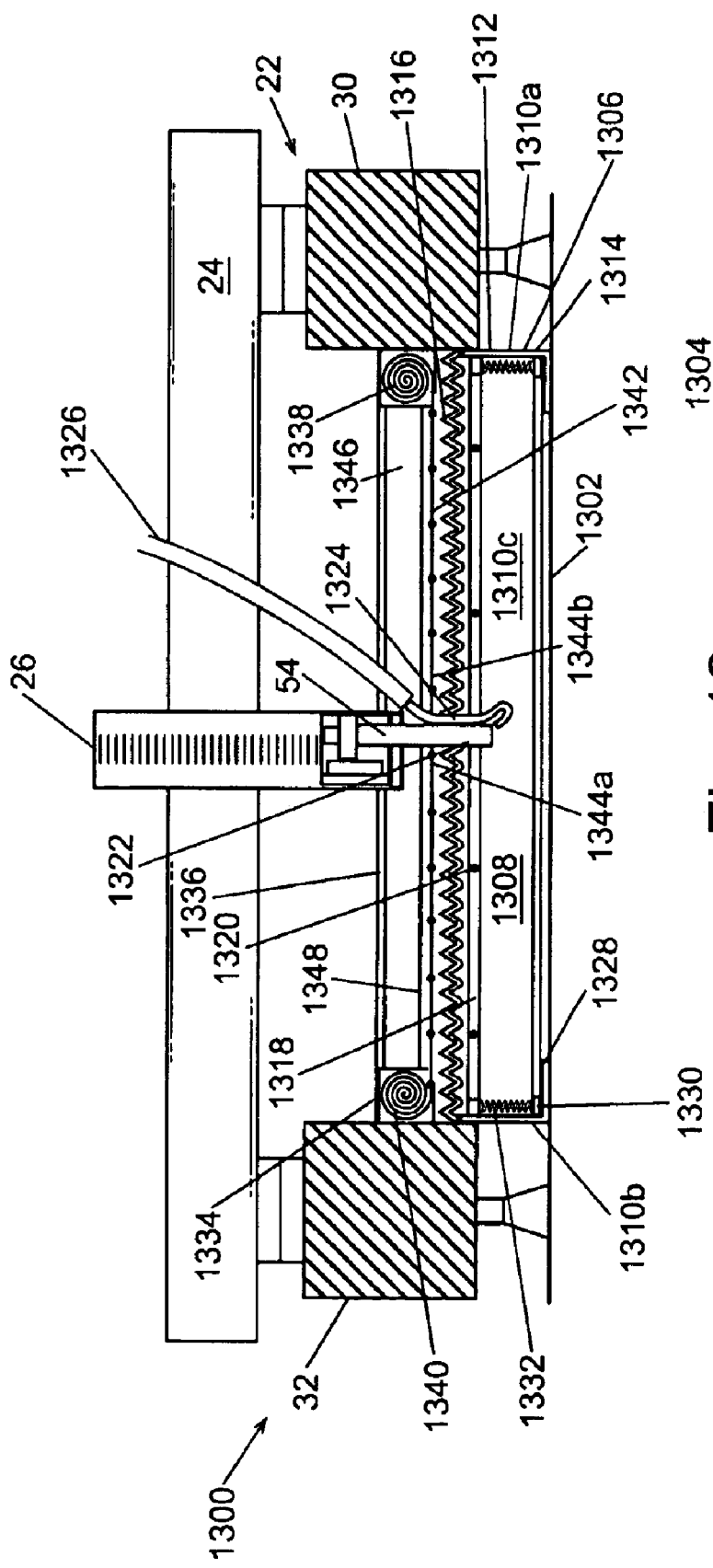
FIG. 13 is cut away view of a fluid bath acoustic coupler.

Referring to FIG. 13, the ASA 14 includes a fluid bath acoustic coupler 1300 for coupling acoustic signals between the acoustic transducer assembly 54 and a surface 1302 of an object 1304. The fluid bath acoustic coupler 1300 includes a fluid holder 1306, which is generally pan shaped having an open interior for holding a fluid 1308. The fluid holder 1306 includes a sidewall 1310, which defines the circumference of the fluid holder 1306 and which includes an upper portion 1312 and a bottom portion 1314, and a top wall 1316 that is attached to the upper portion 1312 of the sidewall 1310.

In this embodiment, the fluid holder 1306 is generally a rectangular shaped pan having right and left sidewalls 1310a and 1310b, respectively and a front sidewall (not shown) and a back sidewall 1310c. In other embodiments, the shape of the fluid holder 1306 is different from rectangular and involves fewer or more sidewalls 1310.

The fluid bath acoustic coupler 1300 also includes a brace 1318, which attaches to the base frame 22 by fasteners 1320, which are typically screws or bolts. Interposing the base frame 22 and the brace 1318 is the sidewall 1310. Thus, the sidewall 1310 is held in place between the brace 1318 and the base frame 22 by attaching the brace 1318 to the base frame 22.

The sidewall 1310 is of sufficient length that in operational position the sidewall 1306 extends from the upper portion 1312 to the bottom portion 1314 such that the bottom portion 1314 makes contact with the surface 1302. Typically, the sidewall 1306 is made from a material that is essentially impermeable to the fluid 1308.

The interior of the fluid holder 1306 is defined by sidewall 1310, which defines a closed circumference, and the top wall 1316, which is attached to the upper portion 1312 of the sidewall 1306 and which essentially covers the area enclosed by the sidewall 1316. The top wall 1316 is made from a material that is essentially impermeable to the fluid 1308 and is pleated in two dimensions. The top wall 1316 is attached to the sidewall 1306 to form an essentially fluid tight seal thereat.

The top wall 1316 defines an opening 1322, which extends through the top wall 1316 and which is in the approximate center of the top wall 1316. The opening 1322 can be moved relative to the right and left sidewalls 1310a and 1310b, respectively, and relative to the front sidewall (not shown) and the rear sidewall 1310c because of the two dimensional pleating in the top wall 1316. The pleats in the top wall 1316 fold and unfold to accommodate the relative movement of the opening 1322.

In one preferred embodiment, the acoustic transducer assembly 54 extends through the opening 1322 such that the face of the acoustic transducer assembly 54 is immersed in the fluid 1308, and the opening 1322 forms an essentially fluid tight seal around the acoustic transducer assembly 54. In one preferred embodiment, a fluid inlet tube 1324, which has an inverted question mark shape is attached to the acoustic transducer assembly 54 such that the hook portion of the question mark is approximately aimed towards the face (see FIG. 10) of the acoustic transducer assembly 54. The fluid inlet tube 1324 is attached to a pressurized fluid hose 1326 and fluid from the hose 1326 flows across the face of the acoustic transducer assembly 54. In one preferred embodiment, the top wall 1316 also includes a relief valve (not shown) through which air escapes from the interior of the fluid holder 1306 as the fluid holder 1306 is filled with fluid.

The fluid bath acoustic coupler 1300 also includes an interior flap that extends from the bottom portion 1314 to the sidewall 1310 therein. The interior flap 1328 is made from a material such as a polymer, which is essentially impervious to the fluid 1308 and which is conformable to the contour of the surface 1302. Hydraulic pressure from the fluid 1308 essentially holds the interior flap 1328 firmly against the surface 1302 to form an essentially fluid type fit around the bottom of the fluid holder 1306.

In one preferred embodiment, the bottom portion 1314 is made from a pliable material that conforms to the contour of the surface 1302 of the object 1304. The bottom portion 1314 also includes a resilient pliable strip 1330, which is pressed towards the surface 1302 by a plurality of springs 1332 that extend from the strip 1330 to the brace 1318. Thus, the bottom portion 1314 is pressed firmly and conformably against the surface 1302 by the strip 1330, which in turn is biased by the springs 1332. With the bottom portion 1314 pressed against the surface 1302, an essentially fluid tight seal is formed between the bottom portion 1314 and the surface 1302.

In operation, the acoustic transducer assembly 54 extends through opening 1322 and is partially immersed in the fluid 1308, which acoustically couples the acoustic transducer assembly 54 to the area of the surface 1302 enclosed by the sidewall 1310. The controller 16 can scan the acoustic transducer assembly 54 over the enclosed area. As the acoustic transducer assembly 54 is scanned over the enclosed area, the acoustic transducer assembly 54 and the opening 1322 move in unison. In response to the movement of the opening 1322, the pleats in the two dimensional pleating of the top wall 1316 fold and unfold to accommodate the movement of the acoustic transducer assembly 54. In addition, the two-dimension pleating of the top wall 1316 accommodate the raising and lowering of the acoustic transducer assembly 54 and pitch and yaw rotations by the rotary devices 56 and 58.

In one preferred embodiment, the fluid bath acoustic coupler 1300 includes a pair of rollable shutter assemblies 1334 and 1336 that essentially cover the top wall 1316. The rollable shutter assembly 1334 that is attached to the support platforms 30 and 32 above the top wall 1316.

The rollable shutter assembly 1334 includes opposed reels 1338 and 1340, which are mounted to the support platforms 30 and 32, respectively, and a shutter 1342. The shutter 1342 is made up of a plurality of slats 1344 that extend partially between the cross members 34a and 34b, and the slats 1344 are hingedly coupled together. Slats 1344a and 1344b are adapted to have a separation distance that is at least the diameter of the acoustic transducer assembly 54 so that the acoustic transducer assembly 54 can extend through shutter 1342. When the controller 16 moves the acoustic transducer assembly left (right) the acoustic transducer assembly 54 engages slat 1344a (1344b) and pushes it in the left (right) direction, thereby causing reel 1340 (reel 1338) to wind and reel 1338 (reel 1340) to unwind shutter 1342.

The rollable shutter assembly 1336 is essentially identical to the rollable shutter assembly 1334, and it includes a front reel (not shown), which is mounted to the cross member 34a, a rear reel 1346, which is mounted to the cross member 34b, and a shutter 1348 that extends from the front reel (not shown) to the rear reel 1346. The shutter 1348 rests upon shutter 1342 and is adapted to slide over shutter 1342.

The shutter 1348 is made up of a plurality of slats, which extend partially between the support platforms 30 and 32 and which are hingedly coupled together. As with the rollable shutter assembly 1334, two of the slats are separated by a distance that is at least the diameter of the acoustic transducer assembly 54. Thus, the shutter 1342 defines a longitudinal gap that extends partially between the cross members 34(*a*) and 34(*b*), and the shutter 1348 defines a transverse gap extending partially between the support platforms 30 and 32.

In operation, the gaps in the rollable shutter assemblies 1334 and 1336 and the opening 1322 are aligned so that the acoustic transducer assembly 54 can extend therethrough. When the acoustic transducer assembly 54 is moved forward (backwards) the acoustic transducer assembly 54 engages a slat of the shutter 1348 and pushes the shutter 1348 forward (rearward), thereby causing the unseen front reel to wind (unwind) and the rear reel 1346 to unwind (wind) the shutter 1348, while the shutter 1342 remains essentially stationary. In one preferred embodiment, the rollable shutter assemblies 1334 and 1336, and the top wall 1316 cooperate such that the acoustic transducer assembly 54 has five degrees of freedom.

In one preferred embodiment, the slats of the shutters 1342 and 1348 are made from a rigid material such as, but not limited to, aluminum. In this embodiment, the rollable shutter assemblies 1334 and 1336 are adapted to support the fluid 1308 contained in the fluid holder 1306 when the fluid bath acoustic coupler 1300 is inverted. Thus, the ASA 14 with the fluid acoustic coupler 1300 attached thereto can be attached to a portion of an object such as the underside of a wing of an aircraft and used for scanning the underside of the wing. In this inverted configuration the weight of fluid 1308 is transferred from the fluid holder 1306 and applied to the rollable shutter assemblies 1334 and 1336.

Although exemplary preferred embodiments of the present invention have been shown and described, it will be apparent to those of ordinary skill in the art that a number of changes, modifications, or alterations to the invention as described may be made, none of which depart from the spirit of the present invention. Changes, modifications, and alterations should therefore be seen as within the scope of the present invention. It should also be emphasized that the above-described embodiments of the present invention, particularly, any "preferred embodiments" are merely possible non-limiting examples of implementations, merely setting forth a clear understanding of the principles of the inventions.

What is claimed is:

1. An apparatus for examining the internal structure of an object by reflection mode scanning acoustic microscopy, the apparatus comprising:
    a base having an extendable arm;
    an acoustic scanning assembly coupled to the arm, the acoustic scanning assembly including:
        a frame having at least one leg extending therefrom, the at least one leg adapted to removably couple to the object, wherein the frame defines a longitudinal direction and a transverse direction; and
        an acoustic transducer assembly moveably coupled to the frame and adapted to move in both the longitudinal and transverse directions; and
        a controller in communication with the acoustic transducer assembly adapted to control the movement of the acoustic transducer assembly;
        a storage device in communication with the acoustic transducer assembly adapted to receive information related to reflected acoustic signals received by the acoustic transducer assembly and store the information therein.

2. The apparatus of claim 1, wherein the base is movable.

3. The apparatus of claim 1, wherein the frame further includes:
- a pair of aligned support platforms, each of the support platforms having a first and a second opposed end; and
- a pair of cross members, one of the cross members extending between the first ends of the pair of the aligned support platforms and the other cross member extending between the second ends of the pair of the aligned support platforms.

4. The apparatus of claim 3, wherein one of the support platforms of the pair of aligned support platforms includes a first linear motor having a first table adapted to slide along that support platform, and the other support platform of the pair of aligned support platforms includes a second linear motor having a second table adapted to slide along that support platform.

5. The apparatus of claim 4, wherein the acoustic scanning assembly further includes:
- a moveable platform having a third moveable table adapted to slide along the moveable platform in the transverse direction, the movable platform fixedly coupled to the first and second tables of the pair of support platforms, wherein the first and second tables slide in the longitudinal direction;
- an arm coupled to the third moveable table, wherein the arm defines an axis; and
- a fourth moveable table slideably coupled to the arm adapted to slide along the arm in the direction of the axis, wherein the acoustic transducer assembly is coupled to the fourth moveable table.

6. The apparatus of claim 5, wherein the acoustic transducer assembly is pivotally coupled to the fourth moveable table.

7. The apparatus of claim 6, further including:
- a first rotary table attached to the fourth moveable table, wherein the first rotary table rotates about a first axis of rotation;
- a second rotary table coupled to the first rotary table, wherein the second rotary table rotates about a second axis of rotation that is approximately perpendicular to the first axis of rotation, and wherein the acoustic transducer assembly is attached to the second rotary table.

8. The apparatus of claim 5, wherein the arm is pivotally coupled to the third table.

9. The apparatus of claim 5, wherein the moveable platform and third moveable table make up a third linear motor, and the arm and the second moveable table make up a fourth linear motor.

10. The apparatus of claim 3, wherein the acoustic scanning assembly further includes:
- a moveable platform slideably mounted to the pair of aligned support platforms, which are aligned approximately parallel, the moveable platform extending therebetween, wherein the moveable platform slides along the pair of aligned support platforms;
- a first moveable table slideably mounted to the moveable platform, wherein the first moveable table slides along the moveable platform in a direction that is transverse to the pair of aligned support platforms;
- an arm fixedly coupled to the first moveable table, wherein the arm defines an axis that is approximately perpendicular the transverse direction; and
- a second moveable table slideably coupled to the arm and slides along the arm in the direction of the axis, wherein the acoustic transducer assembly is coupled to the second moveable table.

11. The apparatus of claim 10, wherein the acoustic transducer assembly is pivotally coupled to the second moveable table.

12. The apparatus of claim 10, wherein the second moveable arm is pivotally coupled to the first moveable arm.

13. The apparatus of claim 1, wherein the object is substantially disposed in air.

14. An apparatus for examining the internal structure of an object by reflection mode scanning acoustic microscopy, the apparatus comprising:
- at least one support platform having a first and a second opposed end and having at least one leg extending therefrom, the at least one leg adapted to removably couple to the object, and wherein the at least one support platform defines a longitudinal direction;
- a first arm coupled to the at least one support platform and extending therefrom, wherein the first arm and the at least one support platform cooperate such that the first arm is slideable along the at least one support platform between the first and second ends of the at least one support platform and defines a transverse direction;
- a second arm coupled to the first arm, wherein the second arm defines an axis, and the first and second arms cooperate such that the second arm is slideable along the first in the transverse direction; and
- an acoustic transducer assembly coupled to the second arm, wherein the acoustic transducer assembly is slideable relative to the second arm in the direction of the axis defined by the second arm.

15. The apparatus of claim 14, wherein the at least one support platform and the first arm cooperate by using a linear motor to slide the first arm along the at least one support platform.

16. The apparatus of claim 14, wherein the at least one support platform and the first arm cooperate by using a rack and pinion assembly to slide the first arm along the at least one support platform.

17. The apparatus of claim 14, wherein the at least one support platform and the first arm cooperate by using piezoelectric motion control to slide the first arm along the at least one support platform.

18. The apparatus of claim 14, wherein the second arm is pivotally coupled to the first arm.

19. The apparatus of claim 14, wherein the acoustic transducer assembly is pivotally coupled to the second arm.

20. The apparatus of claim 14, further including:
- a position controller adapted to send positioning commands to the at least one support platform, the first arm and the second arm, thereby controlling the position of the first arm along the at least one support platform, the position of the second arm along the first arm, and the position of the acoustic transducer assembly along the second arm; and
- a storage device in communication with the acoustic transducer assembly adapted to receive information related to reflected acoustic signals received by the acoustic transducer assembly and store the information therein.

21. The apparatus of claim 20, wherein the position controller uses information related to the surface contour of the object in determining the position commands for the support platform, the first arm and the second arm.

22. The apparatus of claim 20, further including:
- a acoustic transducer assembly controller in communication with the acoustic transducer assembly, wherein the acoustic transducer assembly emits an acoustic signal in response to a signal from the acoustic transducer assembly controller.

23. The apparatus of claim 22, further including:
a controller in communication with the acoustic transducer assembly controller and the position controller, wherein the controller synchronizes the positioning commands from the positioning controller and the signals from the acoustic transducer assembly controller.

24. The apparatus of claim 14, wherein the at least one support platform is a pair of aligned support platforms; and further including:
a pair of cross members, one of the cross members extending between the first ends of the pair of the aligned support platforms and the other cross member extending between the second ends of the pair of the aligned support platforms.

25. The apparatus of claim 24, wherein the at least one leg includes four legs, each of the four legs having a suction cup, wherein two of the four legs extend from one of the pair of support platforms and the other two legs extend from the other support platforms.

26. The apparatus of claim 14, wherein the at least one support platform includes a linear motor having a table adapted to slide along that support platform, and the first arm is fixedly attached to the table.

27. The apparatus of claim 14, wherein the first arm includes a linear motor having a table adapted to slide along the first arm, and the second arm is fixedly attached to the table.

28. The apparatus of claim 14, wherein the second arm includes a linear motor having a table adapted to slide along the second arm, and the acoustic transducer assembly is pivotally attached to the table.

29. The apparatus of claim 14, wherein the object is substantially disposed in air.

30. The apparatus of claim 14, wherein the second arm is pivotally coupled to the first arm.

31. The apparatus of claim 14, wherein the acoustic transducer assembly is pivotally coupled to the second arm.

32. The apparatus of claim 31, wherein the acoustic transducer assembly has five degrees of freedom.

* * * * *